(12) United States Patent
Hilpert et al.

(10) Patent No.: US 9,067,926 B2
(45) Date of Patent: Jun. 30, 2015

(54) FLUOROMETHYL-5,6-DIHYDRO-4H-[1,3]OXAZINES

(71) Applicants: F. Hoffmann-La Roche AG, Basel (CH); Siena Biotech S.p.A., Siena (IT)

(72) Inventors: Hans Hilpert, Muenchenstein (CH); Roland Humm, Auggen (DE); Thomas Woltering, Freiburg (DE)

(73) Assignees: HOFFMANN-LA ROCHE INC., Little Falls, NJ (US); SIENA BIOTECH S.P.A., Siena (IT)

( * ) Notice: Subject to any disclaimer, the term of this patent is extended or adjusted under 35 U.S.C. 154(b) by 0 days.

(21) Appl. No.: 14/373,697

(22) PCT Filed: Jan. 23, 2013

(86) PCT No.: PCT/EP2013/051166
§ 371 (c)(1),
(2) Date: Jul. 22, 2014

(87) PCT Pub. No.: WO2013/110622
PCT Pub. Date: Aug. 1, 2013

(65) Prior Publication Data
US 2015/0031690 A1    Jan. 29, 2015

(30) Foreign Application Priority Data
Jan. 26, 2012 (EP) .................................. 12152686

(51) Int. Cl.
*C07D 265/04* (2006.01)
*C07D 403/12* (2006.01)
*C07D 401/12* (2006.01)
*A61K 31/33* (2006.01)
*C07D 413/12* (2006.01)

(52) U.S. Cl.
CPC ............ *C07D 413/12* (2013.01); *C07D 403/12* (2013.01); *C07D 401/12* (2013.01)

(58) Field of Classification Search
USPC ...................................... 544/88, 96; 514/228.8
See application file for complete search history.

(56) References Cited

U.S. PATENT DOCUMENTS 8,754,075 B2 *    6/2014    Hilpert et al. .............. 514/228.8

* cited by examiner

*Primary Examiner* — Kahsay Habte

(57) ABSTRACT

Provided herein is a compound of formula I:

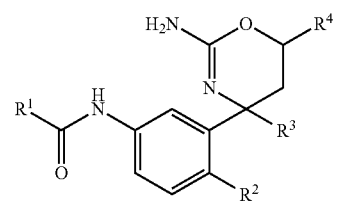

as wells as a pharmaceutical composition, a process of making and a method of using a compound of formula I. The compounds of formula I are BACE1 inhibitors useful for the treatement of, for example, Alzheimer's Disease.

39 Claims, No Drawings

FLUOROMETHYL-5,6-DIHYDRO-4H-[1,3]OXAZINES

This application is a National Stage Application of PCT/EP2013/051166 filed Jan. 23, 2013, which claims priority from European Application No. 12152686.7 filed on Jan. 26, 2012. Each of these applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36):26326). It is thus presumed that inhibitors of BACE1 activity can be useful agents for therapeutic intervention in Alzheimer's disease (AD).

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 can in addition be used to treat the following diseases: IBM (inclusion body myositis) (Vattemi G. et al., Lancet. 2001 Dec. 8; 358(9297):1962-4), Down's Syndrome (Barbiero L. et al, Exp Neurol. 2003 August; 182 (2):335-45), Wilson's Disease (Sugimoto I. et al., J Biol Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., Proc Natl Acad Sci USA 2008 Jan. 29; 105(4):1291-6), Dermatomyositis (Greenberg S. A. et al., Ann Neurol. 2005 May; 57(5):664-78 and Greenberg S. A. et al., Neurol 2005 May; 57(5):664-78), Kaposi Sarcoma (Lagos D. et al, Blood, 2007 Feb. 15; 109(4):1550-8), Glioblastoma multiforme (E-MEXP-2576, http://www.e-bi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmuneinflammatory diseases (Woodard-Grice A. V. et al., J Biol Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljanski J. et al, Thyroid. 2005 July; 15(7):645-52).

The present invention provides novel compounds of formula I, their manufacture, medicaments based on a compound in accordance with the invention and their production as well as the use of compounds of formula I in the control or prevention of illnesses such as Alzheimer's disease. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

FIELD OF THE INVENTION

The present invention provides Fluoromethyl-5,6-dihydro-4H-[1,3]oxazin-2-ylamines having BACE1 inhibitory properties, their manufacture, pharmaceutical compositions containing them and their use as therapeutically active substances.

SUMMARY OF THE INVENTION

The present invention provides a compound of formula I,

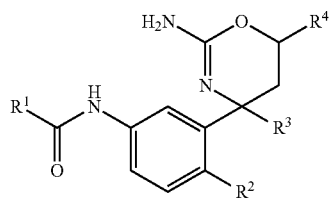

I wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Particular "$C_{1-6}$-alkyl" are "$C_{1-3}$-alkyl". Specific groups are methyl and ethyl. Most specific is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is trifluoromethyl.

The term "cyano-$C_{1-6}$-alkyl", alone or in combination with other groups, refers to $C_{1-6}$-alkyl as defined herein, which is substituted by one or multiple cyano, particularly 1 cyano. Examples are cyanomethyl, cyanoethyl and the like.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$-alkoxy-$C_{1-6}$-alkyl" is methoxy-$C_{1-6}$-alkyl. Examples are methoxymethyl, methoxyethyl and the like.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" is Cl and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl and pyrazinyl, as well as oxazolyl and 1H-pyrazolyl. Specific "heteroaryl" are pyridin-2-yl and pyrazin-2-yl, as well as 1H-pyrazole-3-yl and oxazol-4-yl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), iso-pentyloxy (i-pentyloxy) and the like. Particular "$C_{1-6}$-alkoxy" are groups with 1 to 4 carbon atoms. Specific is methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific "halogen-$C_{1-6}$-alkoxy" is trifluoromethoxy.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, and n-butynyl.

The term "aryl" denotes a monovalent aromatic carbocyclic mono- or bicyclic ring system comprising 6 to 10 carbon ring atoms. Examples of aryl moieties include phenyl and naphthyl. Specific "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" (here also P') denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T.W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

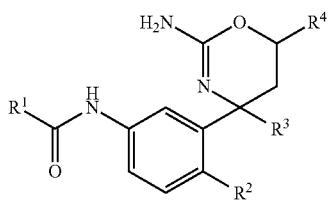

wherein
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl, and
  ii) halogen-$C_{1-6}$-alkyl,
$R^4$ is halogen-$C_{1-6}$-alkyl;
or pharmaceutically acceptable salts thereof.

A certain embodiment of the invention provides a compound of formula Ia,

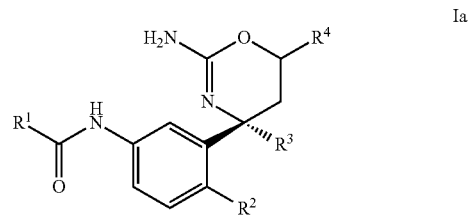

wherein
$R^1$ is selected from the group consisting of
  i) aryl,
  ii) aryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl, and
  ii) halogen-$C_{1-6}$-alkyl,
$R^4$ is halogen-$C_{1-6}$-alkyl;
or pharmaceutically acceptable salts thereof.

A certain embodiment of the invention provides a compound of formula Ic,

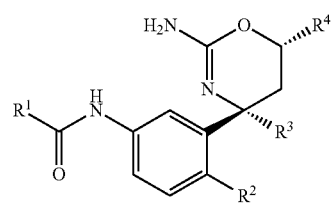

wherein
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl, and
  ii) halogen-$C_{1-6}$-alkyl,
$R^4$ is halogen-$C_{1-6}$-alkyl;
or pharmaceutically acceptable salts thereof.

A certain embodiment of the invention provides a compound of formula Id,

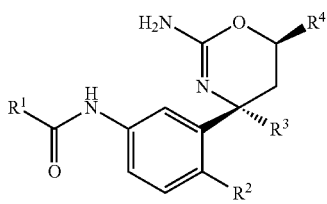

wherein
$R^1$ is selected from the group consisting of
  i) aryl,
  ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
  i) hydrogen,
  ii) $C_{1-6}$-alkyl, and
  iii) halogen;
$R^3$ is selected from the group consisting of
  i) $C_{1-6}$-alkyl, and
  ii) halogen-$C_{1-6}$-alkyl,
$R^4$ is halogen-$C_{1-6}$-alkyl;
or pharmaceutically acceptable salts thereof.

A certain embodiment of the invention provides a compound of formula Ia-1,

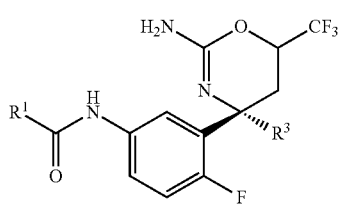

wherein
$R^1$ is selected from the group consisting of
  i) aryl,
  ii) aryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
  iii) heteroaryl, and
  iv) heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl; and
$R^3$ is selected from the group consisting of
  i) $C_{1-6}$-alkyl, and
  ii) halogen-$C_{1-6}$-alkyl,
or pharmaceutically acceptable salts thereof.

A certain embodiment of the invention provides a compound of formula Ia-1',

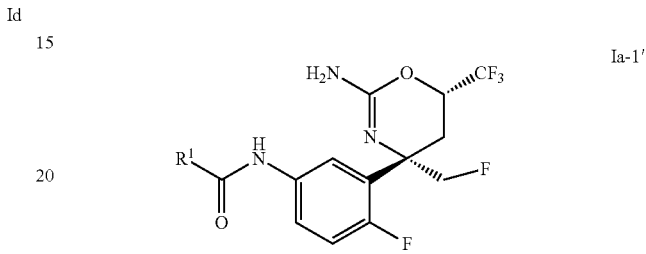

wherein
$R^1$ is heteroaryl substituted by 1-2 substituents individually selected from cyano and halogen,
or pharmaceutically acceptable salts thereof.

A certain embodiment of the invention provides a compound as described herein, wherein $R^2$ is halogen.

A certain embodiment of the invention provides a compound as described herein, wherein $R^2$ is F.

A certain embodiment of the invention provides a compound as described herein, wherein $R^2$ is hydrogen.

A certain embodiment of the invention provides a compound as described herein, wherein $R^2$ is $C_{1-6}$-alkyl.

A certain embodiment of the invention provides a compound as described herein, wherein $R^2$ is methyl.

A certain embodiment of the invention provides a compound as described herein, wherein $R^3$ is halogen-$C_{1-6}$-alkyl.

A certain embodiment of the invention provides a compound as described herein, wherein $R^3$ is fluoro-$C_{1-6}$-alkyl.

A certain embodiment of the invention provides a compound as described herein, wherein $R^3$ is fluoromethyl.

A certain embodiment of the invention provides a compound as described herein, wherein $R^3$ is $C_{1-6}$-alkyl.

A certain embodiment of the invention provides a compound as described herein, wherein $R^3$ is methyl.

A certain embodiment of the invention provides a compound as described herein, wherein $R^4$ is fluoro-$C_{1-6}$-alkyl.

A certain embodiment of the invention provides a compound as described herein, wherein $R^4$ is trifluoromethyl.

A certain embodiment of the invention provides a compound as described herein, wherein $R^1$ is heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_2$-6-alkynyl-$C_{1-6}$-alkoxy, $C_{2-6}$-alkynyl and $C_{1-6}$-alkyl.

A certain embodiment of the invention provides a compound as described herein, wherein $R^1$ is heteroaryl substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.

A certain embodiment of the invention provides a compound as described herein, wherein $R^1$ is heteroaryl substituted by 1-2 substituents individually selected from cyano, halogen, halogen-$C_{1-6}$-alkoxy and $C_{1-6}$-alkoxy.

A certain embodiment of the invention provides a compound as described herein, wherein $R^1$ is pyridinyl or pyrazinyl substituted by 1-2 substituents individually selected from cyano, halogen, halogen-$C_{1-6}$-alkoxy and $C_{1-6}$-alkoxy.

A certain embodiment of the invention provides a compound as described herein, wherein $R^1$ is pyridinyl substituted by cyano.

A certain embodiment of the invention provides a compound as described herein, wherein $R^1$ is pyridinyl substituted by halogen.

A certain embodiment of the invention provides a compound as described herein, wherein $R^1$ is pyridinyl substituted by halogen-$C_{1-6}$-alkoxy.

A certain embodiment of the invention provides a compound as described herein, wherein $R^1$ is pyridinyl substituted by $C_{1-6}$-alkoxy.

A certain embodiment of the invention provides a compound as described herein, wherein $R^1$ is pyridinyl substituted by cyano and $C_{1-6}$-alkyl.

A certain embodiment of the invention provides a compound as described herein, wherein $R^1$ is pyridinyl substituted by cyano and halogen.

A certain embodiment of the invention provides a compound as described herein, wherein $R^1$ is pyridinyl substituted by halogen-$C_{1-6}$-alkyl.

A certain embodiment of the invention provides a compound as described herein, wherein $R^1$ is pyridinyl substituted by $C_{1-6}$-alkyl.

A certain embodiment of the invention provides a compound as described herein, wherein $R^1$ is pyrazinyl substituted by $C_{1-6}$-alkyl.

A certain embodiment of the invention provides a compound as described herein, wherein $R^1$ is pyrazinyl substituted by halogen-$C_{1-6}$-alkoxy.

A certain embodiment of the invention provides a compound as described herein, wherein $R^1$ is pyrazinyl substituted by halogen-$C_{1-6}$-alkyl.

A certain embodiment of the invention provides a compound as described herein, wherein $R^1$ is pyrazinyl substituted by $C_{1-6}$-alkoxy.

A certain embodiment of the invention provides a compound as described herein, wherein $R^1$ is pyrazinyl substituted by $C_{2-6}$-alkynyl-$C_{1-6}$-alkoxy.

A certain embodiment of the invention provides a compound as described herein, wherein $R^1$ is oxazolyl substituted by halogen-$C_{1-6}$-alkyl.

A certain embodiment of the invention provides a compound as described herein, wherein $R^1$ is pyrazolyl substituted by halogen-$C_{1-6}$-alkyl.

A certain embodiment of the invention provides a compound as described herein, wherein $R^1$ is 1-(difluoromethyl)-1H-pyrazole-3-yl, 2-(fluoromethyl)oxazole-4-yl, 3,5-dichloro-pyridin-2-yl, 3-chloro-5-cyanopyridin-2-yl, 3-methylpyrazine-2-yl, 4-chloro-1-(difluoromethyl)-1H-pyrazole-3-yl, 5-(2,2,2-trifluoroethoxy)pyrazine-2-yl, 5-(2,2-difluoroethoxy)pyrazine-2-yl, 5-(but-2-ynyloxy)pyrazine-2-yl, 5-(difluoromethoxy)pyrazine-2-yl, 5-(difluoromethyl)pyrazine-2-yl, 5-(fluoromethoxy)pyrazine-2-yl, 5-(fluoromethyl)pyrazine-2-yl, 5-chloro-pyridin-2-yl, 5-cyano-3-methyl-pyridin-2-yl, 5-cyano-pyridin-2-yl, 5-difluoromethoxy-pyrazin-2-yl, 5-difluoromethoxy-pyridin-2-yl, 5-difluoromethyl-pyridin-2-yl, 5-fluoromethoxy-pyridin-2-yl, 5-methoxy-pyrazin-2-yl, 5-methoxy-pyridin-2-yl, 5-methyl-pyrazine-2-yl, 5-trifluoroethoxy-pyridin-2-yl, 5-trifluoromethoxy-pyrazin-2-yl or 5-trifluoromethoxy-pyridin-2-yl.

A certain embodiment of the invention provides a compound as described herein, wherein $R^1$ is 5-cyano-pydidin-2-yl, 5-chloro-pydidin-2-yl, 5-(2,2-difluoroethoxyl)pyrazine-2-yl, 5-(2,2,2-trifluoroethoxyl)pyrazine-2-yl or 5-methoxypyrazine-2-yl.

A certain embodiment of the invention provides a compound as described herein, wherein $R^1$ is 1-(difluoromethyl)-1H-pyrazole-3-yl.

A certain embodiment of the invention provides a compound as described herein, wherein $R^1$ is 2-(fluoromethyl)oxazole-4-yl.

A certain embodiment of the invention provides a compound as described herein, wherein $R^1$ is 3,5-dichloro-pyridin-2-yl.

A certain embodiment of the invention provides a compound as described herein, wherein $R^1$ is 3-chloro-5-cyanopyridin-2-yl.

A certain embodiment of the invention provides a compound as described herein, wherein $R^1$ is 3-methylpyrazine-2-yl.

A certain embodiment of the invention provides a compound as described herein, wherein $R^1$ is 4-chloro-1-(difluoromethyl)-1H-pyrazole-3-yl.

A certain embodiment of the invention provides a compound as described herein, wherein $R^1$ is 5-(but-2-ynyloxy)pyrazine-2-yl.

A certain embodiment of the invention provides a compound as described herein, wherein $R^1$ is 5-(difluoromethoxy)pyrazine-2-yl.

A certain embodiment of the invention provides a compound as described herein, wherein $R^1$ is 5-(difluoromethyl)pyrazine-2-yl.

A certain embodiment of the invention provides a compound as described herein, wherein $R^1$ is 5-(fluoromethoxy)pyrazine-2-yl.

A certain embodiment of the invention provides a compound as described herein, wherein $R^1$ is 5-(fluoromethyl)pyrazine-2-yl.

A certain embodiment of the invention provides a compound as described herein, wherein $R^1$ is 5-cyano-3-methyl-pyridin-2-yl.

A certain embodiment of the invention provides a compound as described herein, wherein $R^1$ is 5-difluoromethoxy-pyrazin-2-yl.

A certain embodiment of the invention provides a compound as described herein, wherein $R^1$ is 5-difluoromethoxy-pyridin-2-yl.

A certain embodiment of the invention provides a compound as described herein, wherein $R^1$ is 5-difluoromethyl-pyridin-2-yl.

A certain embodiment of the invention provides a compound as described herein, wherein $R^1$ is 5-fluoromethoxy-pyridin-2-yl.

A certain embodiment of the invention provides a compound as described herein, wherein $R^1$ is 5-methoxy-pyridin-2-yl.

A certain embodiment of the invention provides a compound as described herein, wherein $R^1$ is 5-methyl-pyrazine-2-yl.

A certain embodiment of the invention provides a compound as described herein, wherein $R^1$ is 5-trifluoroethoxy-pyridin-2-yl.

A certain embodiment of the invention provides a compound as described herein, wherein $R^1$ is 5-trifluoromethoxy-pyrazin-2-yl.

A certain embodiment of the invention provides a compound as described herein, wherein $R^1$ is 5-trifluoromethoxy-pyridin-2-yl.

A certain embodiment of the invention provides a compound as described herein, wherein R¹ is 5-cyano-pydidin-2-yl, A certain embodiment of the invention provides a compound as described herein, wherein R¹ is 5-chloro-pydidin-2-yl.

A certain embodiment of the invention provides a compound as described herein, wherein R¹ is 5-(2,2-difluoroethoxyl)pyrazine-2-yl.

A certain embodiment of the invention provides a compound as described herein, wherein R¹ is 5-(2,2,2-trifluoroethoxyl)pyrazine-2-yl.

A certain embodiment of the invention provides a compound as described herein, wherein R¹ is 5-methoxypyrazine-2-yl.

A certain embodiment of the invention provides a compound as described herein, selected from the group consisting of N-(3-((4S,6S)-2-amino-4-methyl-6-(trifluoromethyl)-5,6-dihydro-4H-1,3-oxazin-4-yl)-4-fluorophenyl)-5-cyanopicolinamide, N-(3-((4S,6S)-2-amino-4-methyl-6-(trifluoromethyl)-5,6-dihydro-4H-1,3-oxazin-4-yl)-4-fluorophenyl)-5-chloropicolinamide, N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide, N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide, N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide, N-(3-((4S,6S)-2-amino-4-methyl-6-(trifluoromethyl)-5,6-dihydro-4H-1,3-oxazin-4-yl)-4-fluorophenyl)-5-(2,2-difluoroethoxyl)pyrazine-2-carboxamide, N-(3-((4S,6S)-2-amino-4-methyl-6-(trifluoromethyl)-5,6-dihydro-4H-1,3-oxazin-4-yl)-4-fluorophenyl)-5-(2,2,2-trifluoro ethoxy)pyrazine-2-carboxamide, N-(3-((4S,6R)-2-Amino-4-methyl-6-(trifluoromethyl)-5,6-dihydro-4H-1,3-oxazin-4-yl)-4-fluorophenyl)-5-cyanopicolinamide, N-(3-((4S,6R)-2-Amino-4-methyl-6-(trifluoromethyl)-5,6-dihydro-4H-1,3-oxazin-4-yl)-4-fluorophenyl)-5-chloropicolinamide, N-(3-((4S,6S)-2-Amino-4-methyl-6-(trifluoromethyl)-5,6-dihydro-4H-1,3-oxazin-4-yl)-4-fluorophenyl)-3,5-chloropicolinamide, N-(3-((4S,6S)-2-Amino-4-methyl-6-(trifluoromethyl)-5,6-dihydro-4H-1,3-oxazin-4-yl)-4-fluorophenyl)-5-(fluoromethoxy)picolinamide, N-(3-((4S,6S)-2-Amino-4-methyl-6-(trifluoromethyl)-5,6-dihydro-4H-1,3-oxazin-4-yl)-4-fluorophenyl)-5-cyano-3-methylpicolinamide, N-(3-((4S,6S)-2-Amino-4-methyl-6-(trifluoromethyl)-5,6-dihydro-4H-1,3-oxazin-4-yl)-4-fluorophenyl)-3-chloro-5-cyanopicolinamide, N-(3-((4S,6S)-2-Amino-4-methyl-6-(trifluoromethyl)-5,6-dihydro-4H-1,3-oxazin-4-yl)-4-fluorophenyl)-5-methoxypicolinamide, N-(3-((4S,6S)-2-Amino-4-methyl-6-(trifluoromethyl)-5,6-dihydro-4H-1,3-oxazin-4-yl)-4-fluorophenyl)-5-(difluoromethoxy)picolinamide, N-(3-((4S,6S)-2-Amino-4-methyl-6-(trifluoromethyl)-5,6-dihydro-4H-1,3-oxazin-4-yl)-4-fluorophenyl)-5-(trifluoromethoxy)picolinamide, N-(3-((4S,6S)-2-Amino-4-methyl-6-(trifluoromethyl)-5,6-dihydro-4H-1,3-oxazin-4-yl)-4-fluorophenyl)-5-(difluoromethyl)picolinamide, N-(3-((4S,6S)-2-Amino-4-methyl-6-(trifluoromethyl)-5,6-dihydro-4H-1,3-oxazin-4-yl)-4-fluorophenyl)-5-(2,2,2-trifluoroethoxy)picolinamide, N-(3-((4S,6S)-2-Amino-4-methyl-6-(trifluoromethyl)-5,6-dihydro-4H-1,3-oxazin-4-yl)-4-fluorophenyl)-5-(fluoromethyl)pyrazine-2-carboxamide, N-(3-((4S,6S)-2-Amino-4-methyl-6-(trifluoromethyl)-5,6-dihydro-4H-1,3-oxazin-4-yl)-4-fluorophenyl)-5-(difluoromethyl)pyrazine-2-carboxamide, N-(3-((4S,6S)-2-Amino-4-methyl-6-(trifluoromethyl)-5,6-dihydro-4H-1,3-oxazin-4-yl)-4-fluorophenyl)-5-methylpyrazine-2-carboxamide, N-(3-((4S,6S)-2-Amino-4-methyl-6-(trifluoromethyl)-5,6-dihydro-4H-1,3-oxazin-4-yl)-4-fluorophenyl)-5-(but-2-ynyloxy)pyrazine-2-carboxamide, N-(3-((4S,6S)-2-Amino-4-methyl-6-(trifluoromethyl)-5,6-dihydro-4H-1,3-oxazin-4-yl)-4-fluorophenyl)-5-(fluoromethoxy)pyrazine-2-carboxamide, N-(3-((4S,6S)-2-Amino-4-methyl-6-(trifluoromethyl)-5,6-dihydro-4H-1,3-oxazin-4-yl)-4-fluorophenyl)-5-(difluoromethoxy)pyrazine-2-carboxamide, N-(3-((4S,6S)-2-Amino-4-methyl-6-(trifluoromethyl)-5,6-dihydro-4H-1,3-oxazin-4-yl)-4-fluorophenyl)-2-(fluoromethyl)oxazole-4-carboxamide, N-(3-((4S,6S)-2-Amino-4-methyl-6-(trifluoromethyl)-5,6-dihydro-4H-1,3-oxazin-4-yl)-4-fluorophenyl)-4-chloro-1-(difluoromethyl)-1H-pyrazole-3-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-cyano-3-methylpicolinamide, N-(3-((4S,6S)-2-Amino-4-(fluoromethyl)-6-(trifluoromethyl)-5,6-dihydro-4H-1,3-oxazin-4-yl)-4-fluorophenyl)-3-chloro-5-cyanopicolinamide, N-(3-((4S,6S)-2-Amino-4-(fluoromethyl)-6-(trifluoromethyl)-5,6-dihydro-4H-1,3-oxazin-4-yl)-4-fluorophenyl)-3,5-dichloropicolinamide, N-(3-((4S,6S)-2-Amino-4-(fluoromethyl)-6-(trifluoromethyl)-5,6-dihydro-4H-1,3-oxazin-4-yl)-4-fluorophenyl)-5-methoxypicolinamide, N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethoxy)picolinamide, N-(3-((4S,6S)-2-Amino-4-(fluoromethyl)-6-(trifluoromethyl)-5,6-dihydro-4H-1,3-oxazin-4-yl)-4-fluorophenyl)-5-(trifluoromethoxy)picolinamide, N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethyl)picolinamide, N-(3-((4S,6S)-2-Amino-4-(fluoromethyl)-6-(trifluoromethyl)-5,6-dihydro-4H-1,3-oxazin-4-yl)-4-fluorophenyl)-5-(2,2,2-trifluoroethoxy)picolinamide, N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethoxy)picolinamide, N-(3-((4S,6S)-2-Amino-4-(fluoromethyl)-6-(trifluoromethyl)-5,6-dihydro-4H-1,3-oxazin-4-yl)-4-fluorophenyl)-5-methoxypyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethyl)ypyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(but-2-ynyloxy)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethoxy)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(2,2-difluoroethoxy)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(2,2,2- trifluoroethoxy)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-methylpyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethoxy)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-3-methylpyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethyl)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-4-chloro-1-(difluoromethyl)-1H-pyrazole-3-carboxamide, N-(3-((4S,6S)-2-Amino-4-(fluoromethyl)-6-(trifluoromethyl)-5,6-dihydro-4H-1,3-oxazin-4-yl)-4-fluorophenyl)-2-(fluoromethyl)oxazole-4-carboxamide, N-(3-((4S,6R)-2-Amino-4-(difluoromethyl)-6-(trifluoromethyl)-5,6-dihydro-4H-1,3-oxazin-4-yl)-4-fluorophenyl)-5-cyanopicolinamide and N-(3-((4S,6S)-2-Amino-4-(difluoromethyl)-6-(trifluoromethyl)-5,6-dihydro-4H-1,3-oxazin-4-yl)-4-fluorophenyl)-5-cyanopicolinamide.

or a pharmaceutically acceptable salt thereof.

A certain embodiment of the invention provides a compound as described herein, selected from the group consisting of N-(3-((4S,6S)-2-amino-4-methyl-6-(trifluoromethyl)-5,6-dihydro-4H-1,3-oxazin-4-yl)-4-fluorophenyl)-5-cyanopicolinamide, N-(3-((4S,6S)-2-amino-4-methyl-6-(trifluoromethyl)-5,6-dihydro-4H-1,3-oxazin-4-yl)-4-fluorophenyl)-5-chloropicolinamide, N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide, N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide, N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide, N-(3-((4S,6S)-2-amino-4-methyl-6-(trifluoromethyl)-5,6-dihydro-4H-1,3-oxazin-4-yl)-4-fluorophenyl)-5-(2,2-difluoroethoxyl)pyrazine-2-carboxamide, and N-(3-((4S,6S)-2-amino-4-methyl-6-(trifluoromethyl)-5,6-dihydro-4H-1,3-oxazin-4-yl)-4-fluorophenyl)-5-(2,2,2-trifluoroethoxy)pyrazine-2-carboxamide, or a pharmaceutically acceptable salt thereof.

A certain embodiment of the invention provides a compound as described herein, which is N-(3-((4S,6S)-2-amino-4-methyl-6-(trifluoromethyl)-5,6-dihydro-4H-1,3-oxazin-4-yl)-4-fluorophenyl)-5-cyanopicolinamide.

A certain embodiment of the invention provides a compound as described herein, which is N-(3-((4S,6S)-2-amino-4-methyl-6-(trifluoromethyl)-5,6-dihydro-4H-1,3-oxazin-4-yl)-4-fluorophenyl)-5-chloropicolinamide.

A certain embodiment of the invention provides a compound as described herein, which is N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide.

A certain embodiment of the invention provides a compound as described herein, which is N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide.

A certain embodiment of the invention provides a compound as described herein, which is N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide.

A certain embodiment of the invention provides a compound as described herein, which is N-(3-((4S,6S)-2-amino-4-methyl-6-(trifluoromethyl)-5,6-dihydro-4H-1,3-oxazin-4-yl)-4-fluorophenyl)-5-(2,2-difluoroethoxyl)pyrazine-2-carboxamide, and A certain embodiment of the invention provides a compound as described herein, which is N-(3-((4S,6S)-2-amino-4-methyl-6-(trifluoromethyl)-5,6-dihydro-4H-1,3-oxazin-4-yl)-4-fluorophenyl)-5-(2,2,2-trifluoroethoxyl)pyrazine-2-carboxamide.

A certain embodiment of the invention provides a process comprises reacting a compound of formula XI' with a compound of formula XII' to a compound of formula I.

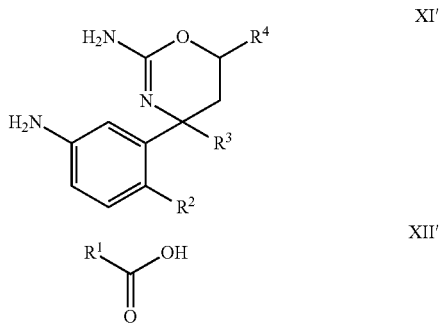

wherein $R^1$, $R^2$, $R^3$ and $R^4$ are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

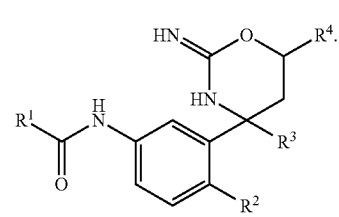

Ie

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Stereoisomers of compounds of formula I are compounds of formula Ia or compounds of formula Ib, in particular compounds of formula Ia, wherein the residues have the meaning as described in any of the embodiments.

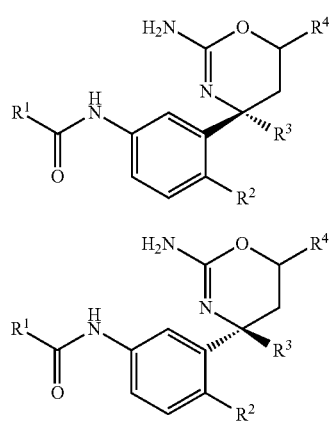

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the following schemes. The starting material is commercially available or may be prepared in accordance with known methods. Any previously defined residues and variables will continue to have the previously defined meaning unless otherwise indicated.

An alkyl-2-chloro-2-(hydroxyimino)acetate is reacted with an olefin in the presence of a base such as an alkyl amine, more particular TEA (triethylamine) or an alkali carbonate, more particular NaHCO$_3$ (sodium hydrogencarbonate) in a solvent such as chlorinated alkanes, in particular CH$_2$Cl$_2$ (dichloromethane) or an ester, in particular AcOEt (ethyl acetate) to give the ester II.

The ester II is reduced with a hydride, in particular NaBH$_4$ (sodium borohydride) in a solvent such as an alcohol, in particular EtOH t(ethanol) give the alcohol III.

A nitro compound is reacted with an olefine in the presence of an activating reagent such as e.g. an isocyanate, in particular phenylisocyanate, and a catalytic amount of a base, in particular an alkyl amine, more particular TEA, in a solvent such as benzene or toluene, in particular benzene, or an alkyl ether, in particular diethyl ether to give the dihydroisoxazole IV wherein R$^3$ is alkyl, particularly methyl.

Dihydroisoxazoles IV wherein R$^3$ is halogen-alkyl, particularly fluoromethyl can be obtained from alcohols III by reaction with a fluorinating agent like e.g. morpholinosulfur trifluoride in an inert solvent like halogenalkanes, preferably dichloromethane, at temperatures between −78° C. and ambient temperature.

Arylation of the dihydroisoxazole IV with the arylbromide V to give the isoxazolidine VI is performed by reacting an arylhalogenide, in particular an arylbromide with an alkyl lithium reagent, in particular n-BuLi to give an aryllithium species, which can be reacted with the dihydroisoxazole IV in the presence of a Lewis base, preferably boron trifluoride etherate in a solvent mixture consisting of an ether, in particular THF (tetrahydrofuran) and toluene at −100° C. to −20° C., in particular at −78° C.

Resolution of the racemic isoxazolidine VI to give the chiral isoxazolidine VII can be done by chiral high-performance liquid chromatography (HPLC) using a Chiralpack AD or Reprosil NR column in a mixture of n-heptane and ethanol or isopropanol as the eluent.

Hydrogenolysis of the chiral isoxazolidine VII to the aminoalcohol VIII can be accomplished best by transfer hydrogenolysis using a Pd-catalyst, in particular Pd on carbon and a hydrogen source, e.g. a salt of formic acid, in particular ammonium formate in a protic solvent such as an alcohol, in particular ethanol.

Oxazine IX can be prepared by reaction of aminoalcohol VIII with cyanogen bromide in a solvent such as an alcohol, in particular ethanol at elevated temperature. Alternatively, the reaction can be carried out in a two step sequenze using cyanogen bromide and a buffer such as e.g. sodium acetate in the presence of a solvent such as e.g. CH$_3$CN followed by cyclisation of the intermediate in the presence of a mineral acid, in particular hydrochloric acid in a solvent such as an ether, in particular 1,4-dioxane.

The nitration of the oxazine (IX to give the nitro-oxazine X follows a standard procedure involving neat sulfuric acid and fuming nitric acid without using a solvent.

The reduction of the nitro group in the intermediate X to give the aniline XI can be accomplished by hydrogenation using a catalyst such as Pd on carbon in protic solvents, such as alcohols, in particular ethanol or methanol.

Selective amide coupling of the aniline XI and a carboxylic acid XII to give the amide I can be effected with 4-(4,6-dimethoxy[1.3.5]triazin-2-yl)-4-methylmorpholinium chloride (DMTMM) hydrate as the condensating agent in a solvent such as an alcohol, in particular methanol.

Scheme 1: Synthesis of compounds of formula Ia-1

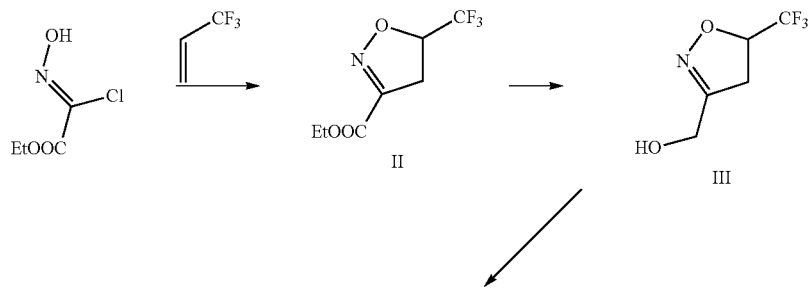

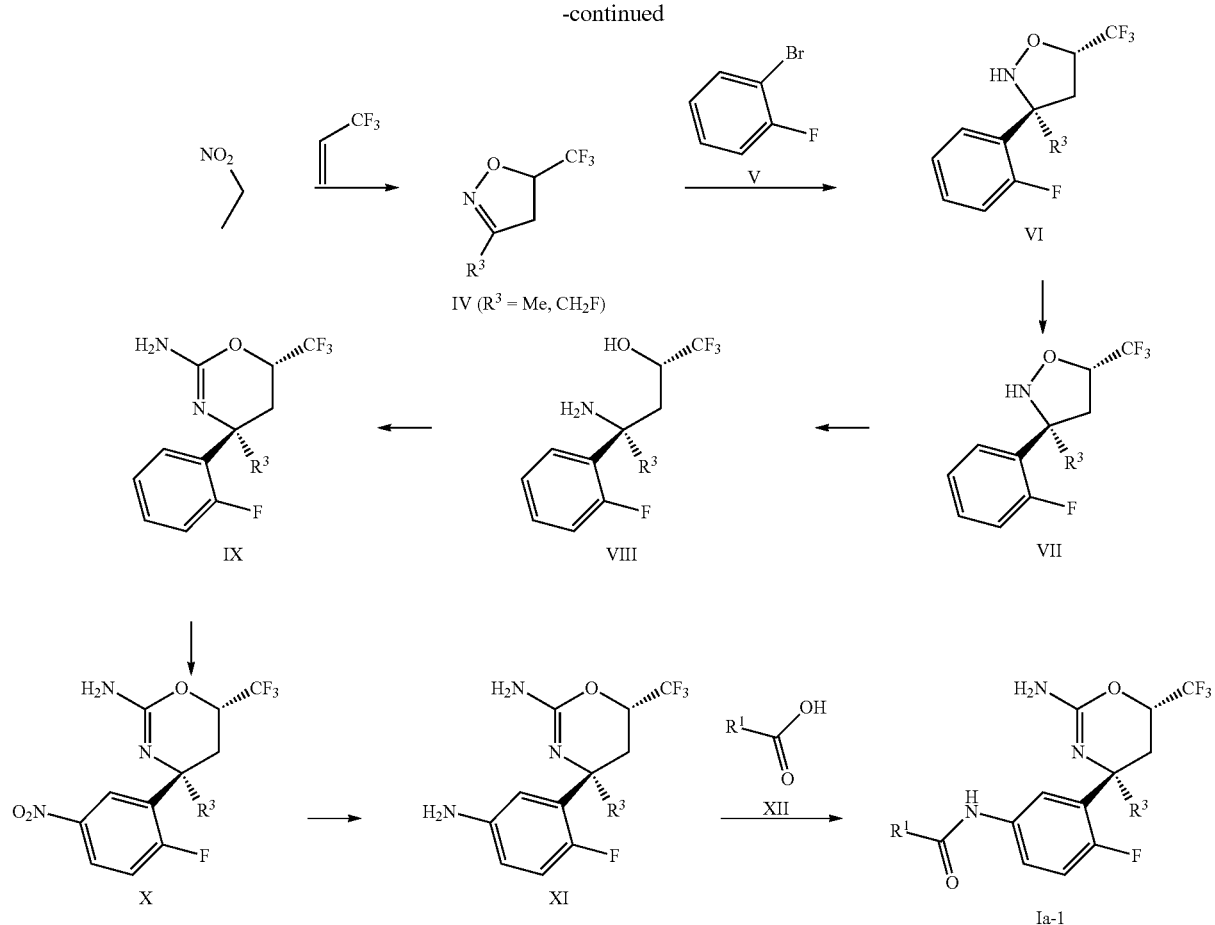

Compounds of formula Ia'-1 can be prepared in accordance with the following Scheme 2.

Sulfinyl imines of general formula XIV can be prepared in analogy to T. P. Tang & J. A. Ellman, J. Org. Chem. 1999, 64, 12, by condensation of an aryl ketone XIII and a sulfinamide, e.g. an alkyl sulfinamide, most particularly (R)-tert-butylsulfinamide or (S)-tert-butylsulfinamide, in the presence of a Lewis acid such as e.g. a titanium(IV)alkoxide, more particularly titanium(IV)ethoxide, in a solvent such as an ether, e.g. diethyl ether or more particularly tetrahydrofuran.

The conversion of the sulfinyl imine XIV to the sulfinamide ester XV proceeds stereoselectively by the chiral directing group as described by Tang & Ellman. The sulfinyl imine XIV can be reacted in a Reformatsky reaction with a zinc enolate, generated from an alkyl acetate substituted by halogen, e.g. particularly ethyl bromoacetate and activated zinc powder, at ambient to elevated temperature, particularly at 23 to 60° C. in a solvent such as an ether, e.g. diethyl ether or more particularly tetrahydrofuran in presence of a copper(I) salt, preferably copper(I) chloride.

Aldehydes of formula XVI can be prepared by the reduction of an ethylester of formula XV with an alkali hydride, e.g. lithium aluminium hydride in presence of diethylamine or sodium dihydrobis(2-methoxyethoxy)aluminate (Red-Al), preferably with diisobutylaluminum hydride (DIBAH) in an inert solvent such as an ether, e.g. diethyl ether or more particularly tetrahydrofuran or in a chlorinated solvent, such as dichloromethane, at temperatures between −78° C. and ambient temperature.

Alcohols of formula XVII can be obtained by the reaction of aldehydes of formula XVI with a trifluoromethylating agent, preferably trifluoromethyltrimethylsilane (Ruppert-Prakash reagent), in presence of tetrabutylammonium fluoride in a solvent such as an ether, e.g. diethyl ether or more particularly tetrahydrofuran, at temperatures between 10° C. and ambient temperature.

Hydrolysis of the chiral directing group in the sulfinamide alcohol of formula XVII to give the aminoalcohol of formula XVIII can be accomplished with a mineral acid, e.g. sulfuric acid or particularly hydrochloric acid, in a solvent such as an ether, e.g. diethyl ether, tetrahydrofuran or more particularly 1,4-dioxane.

The aminooxazine of formula XIX can be prepared by reaction of an aminoalcohol of formula XVIII with cyanogen bromide in a solvent such as an alcohol, particularly ethanol.

The nitro derivative of formula XX can be prepared by nitration of the oxazine XIX following a standard procedure involving neat sulfuric acid and fuming nitric acid without using a solvent.

The reduction of the nitro group in compounds of formula XX to give anilines of formula XXI can be accomplished by hydrogenation using a catalyst, such as palladium on carbon, in protic solvents, such as alcohols, in particular ethanol or methanol.

Selective reaction of anilines of formula XXI with carboxylic acids of formula XII to give amides of formula Ia'-1 can be effected with 4-(4,6-dimethoxy[1.3.5]triazin-2-yl)-4-methylmorpholinium chloride hydrate (DMTMM) as the condensating agent in a solvent such as methanol at temperatures between 0° C. and ambient temperature. Alternatively, 2,4,6-tripropyl-1,3,5,2,4,6-trioxatriphosphorinane-2,4,6-trioxide (T₃P®) can be used as the condensating agent in an inert solvent like e.g. ethyl acetate, at temperatures between 0° C. and ambient temperature.

materials are commercially available, known in the art or can be prepared by methods known in the art or in analogy thereto.

It will be appreciated that the compounds of general formula I in this invention may be derivatised at functional

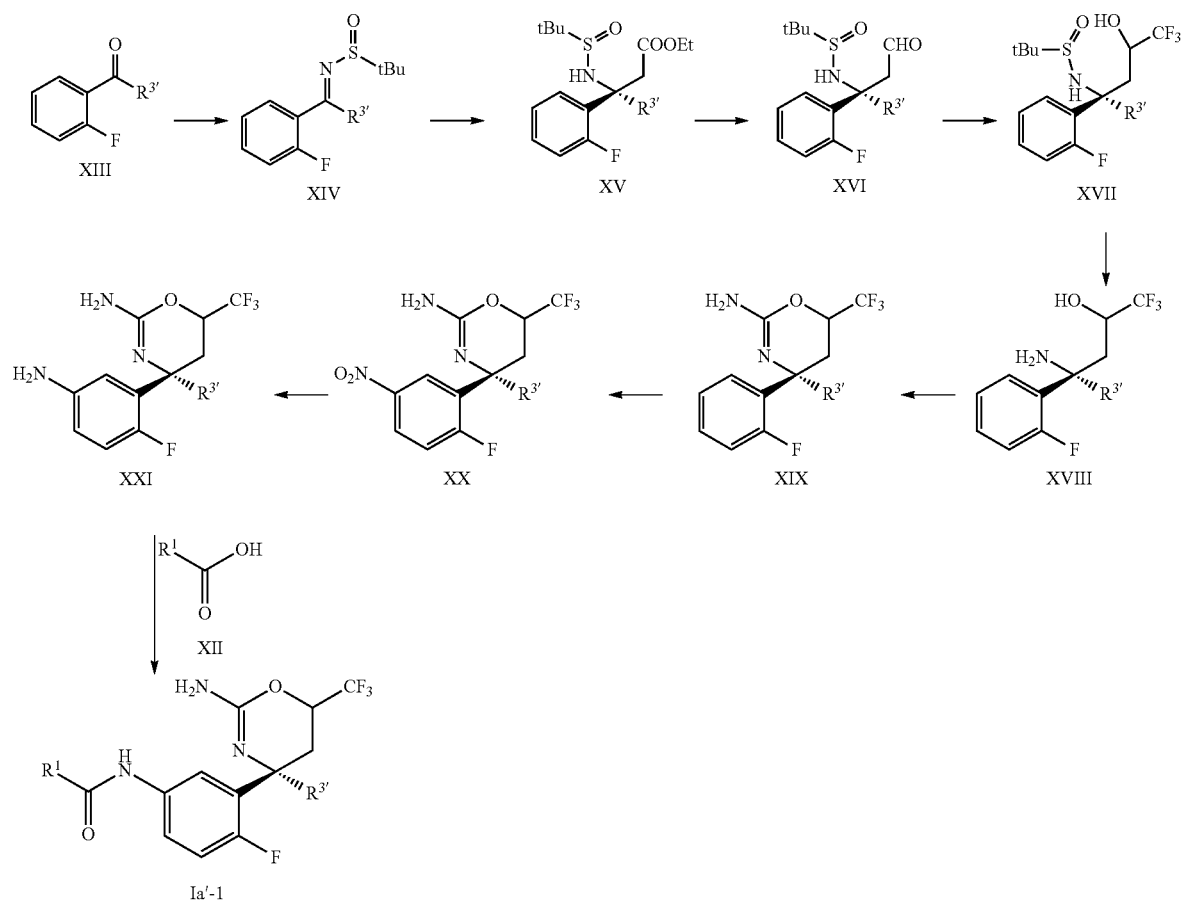

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate. Specific is hydrochloride.

Insofar as their preparation is not described in the examples, the compounds of formula I as well as all intermediate products can be prepared according to analogous methods or according to the methods set forth herein. Starting groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-Lowering Assay:

The Abeta 40 AlphaLISA Assay can be used. The HEK293 APP cells were seeded in 96 well Microtiter plates in cell culture medium (Iscove's, plus 10% (vv) fetal bovine serum, penicillinstreptomycin) to about 80% confluency and the compounds were added at a 3× concentration in 13 volume of culture medium (final DMSO concentration was kept at 1% vv). After 18-20 hrs incubation at 37° C. and 5% CO₂ in a humidified incubator, the culture supernatants were harvested for the determination of Aβ 40 concentrations using Perkin-Elmer Human Amyloid beta 1-40 (high specificity) Kit (Cat# AL275C).

In a Perkin-Elmer White Optiplate-384 (Cat#6007290), 2 ul culture supernatants were combined with 2 µl of a 10× AlphaLISA Anti-hAβAcceptor beads+Biotinylated Antibody Anti-Aβ 1-40 Mix (50 µg/mL/5 nM). After 1 hour room temperature incubation, 16 µl of a 1.25× preparation of Streptavidin (SA) Donor beads (25 µg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The $IC_{50}$ values were calculated using the Excel XLfit software.

TABLE 1

| Exam. | Structure | BACE1 cell act. Aβ40 $IC_{50}$ [nM] |
|---|---|---|
| 1 | 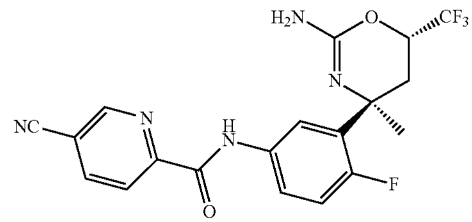 [SMILES: C[C@@]1(c2cc(NC(=O)c3ccc(C#N)cn3)ccc2F)C[C@@H](C(F)(F)F)OC(N)=N1] | 2 |
| 2 | 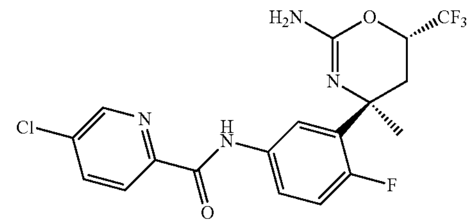 [SMILES: C[C@@]1(c2cc(NC(=O)c3ccc(Cl)cn3)ccc2F)C[C@@H](C(F)(F)F)OC(N)=N1] | 5 |
| 3 | 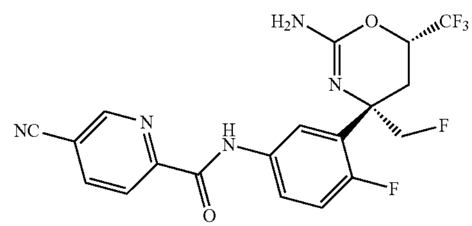 [SMILES: N#Cc1ccc(C(=O)Nc2ccc(F)c([C@]3(CF)C[C@@H](C(F)(F)F)OC(N)=N3)c2)nc1] | 13 |
| 4 | 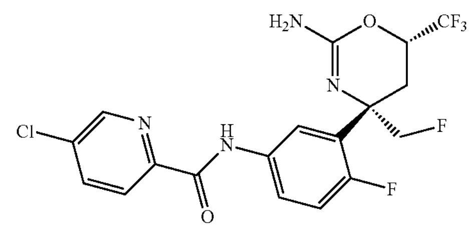 [SMILES: NC1=N[C@](CF)(c2cc(NC(=O)c3ccc(Cl)cn3)ccc2F)C[C@@H](C(F)(F)F)O1] | 22 |
| 5 | 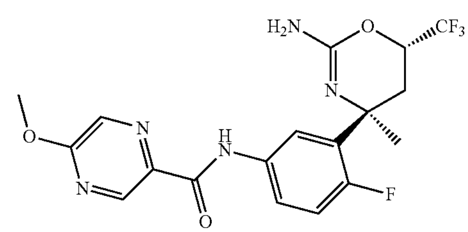 | 5 |
| 6 | 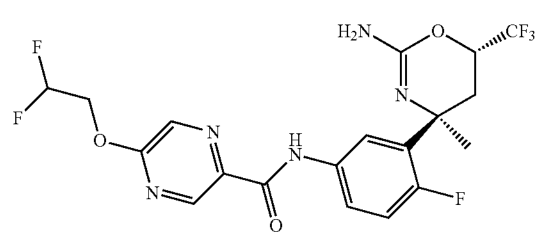 [SMILES: C[C@@]1(c2cc(NC(=O)c3cnc(OCC(F)F)cn3)ccc2F)C[C@@H](C(F)(F)F)OC(N)=N1] | 24 |

TABLE 1-continued

IC₅₀ values of selected examples

| Exam. | Structure | BACE1 cell act. Aβ40 IC₅₀ [nM] |
|---|---|---|
| 7 | 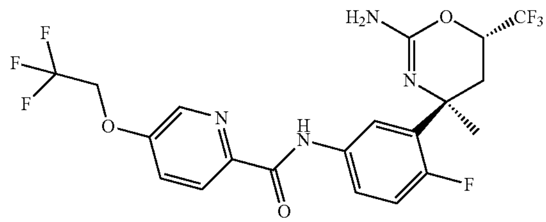 [SMILES: C[C@@]1(c2cc(NC(=O)c3ccc(OCC(F)(F)F)cn3)ccc2F)C[C@@H](C(F)(F)F)OC(N)=N1] | 15 |
| 8 | 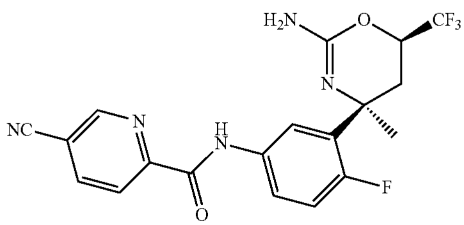 [SMILES: C[C@@]1(c2cc(NC(=O)c3ccc(C#N)cn3)ccc2F)C[C@H](C(F)(F)F)OC(N)=N1] | 230 |
| 9 | 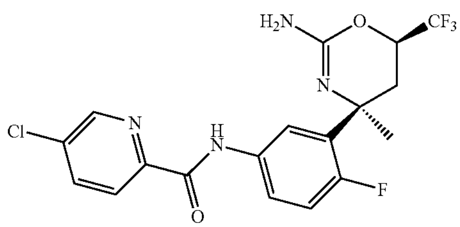 [SMILES: C[C@@]1(c2cc(NC(=O)c3ccc(Cl)cn3)ccc2F)C[C@H](C(F)(F)F)OC(N)=N1] | 710 |
| 10 | 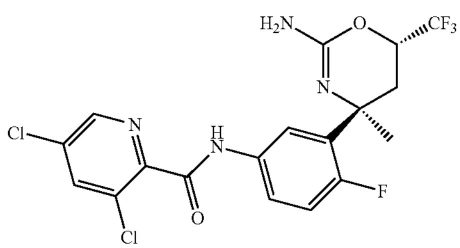 [SMILES: C[C@@]1(c2cc(NC(=O)c3ncc(Cl)cc3Cl)ccc2F)C[C@@H](C(F)(F)F)OC(N)=N1] | 6 |
| 11 | 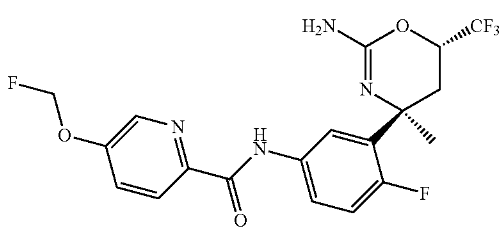 [SMILES: C[C@@]1(c2cc(NC(=O)c3ccc(OCF)cn3)ccc2F)C[C@@H](C(F)(F)F)OC(N)=N1] | 4 |
| 12 | 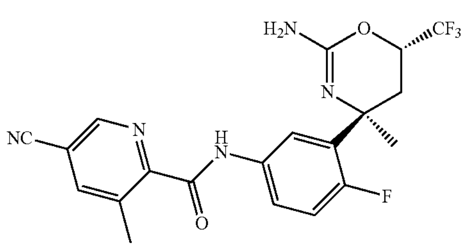 [SMILES: Cc1cc(C#N)cnc1C(=O)Nc1ccc(F)c([C@]2(C)C[C@@H](C(F)(F)F)OC(N)=N2)c1] | 3 |

TABLE 1-continued

IC₅₀ values of selected examples

| Exam. | Structure | BACE1 cell act. Aβ40 IC₅₀ [nM] |
|---|---|---|
| 13 | 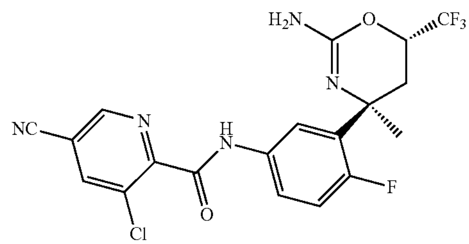 [SMILES: C[C@@]1(c2cc(NC(=O)c3ncc(C#N)cc3Cl)ccc2F)C[C@@H](C(F)(F)F)OC(N)=N1] | 13 |
| 14 | 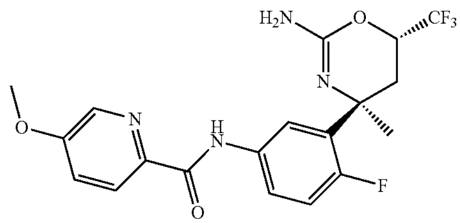 [SMILES: COc1ccc(C(=O)Nc2ccc(F)c([C@]3(C)C[C@@H](C(F)(F)F)OC(N)=N3)c2)nc1] | 2 |
| 15 | 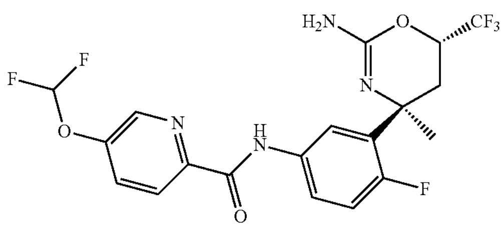 [SMILES: C[C@@]1(c2cc(NC(=O)c3ccc(OC(F)F)cn3)ccc2F)C[C@@H](C(F)(F)F)OC(N)=N1] | 1 |
| 16 | 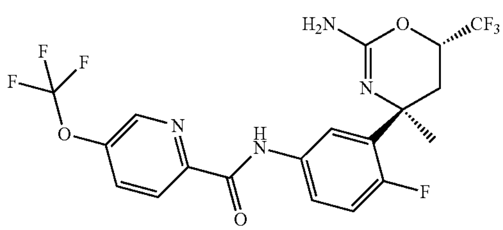 [SMILES: C[C@@]1(c2cc(NC(=O)c3ccc(OC(F)(F)F)cn3)ccc2F)C[C@@H](C(F)(F)F)OC(N)=N1] | 1 |
| 17 | 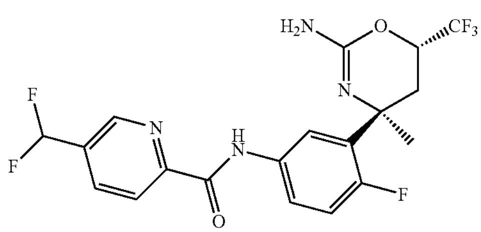 [SMILES: C[C@@]1(c2cc(NC(=O)c3ccc(C(F)F)cn3)ccc2F)C[C@@H](C(F)(F)F)OC(N)=N1] | 2 |
| 18 | 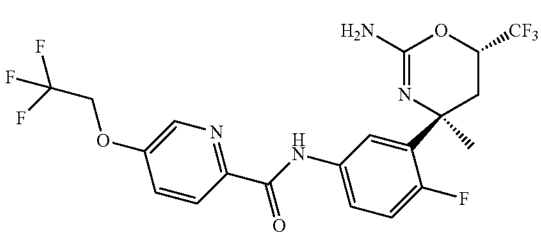 [SMILES: C[C@@]1(c2cc(NC(=O)c3ccc(OCC(F)(F)F)cn3)ccc2F)C[C@@H](C(F)(F)F)OC(N)=N1] | 8 |

TABLE 1-continued

IC$_{50}$ values of selected examples

| Exam. | Structure | BACE1 cell act. Aβ40 IC$_{50}$ [nM] |
|---|---|---|
| 19 | 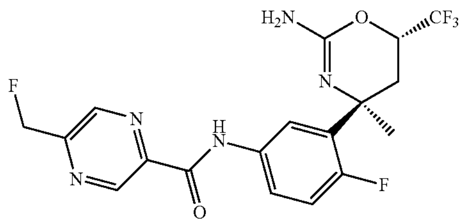 [SMILES: C[C@@]1(c2cc(NC(=O)c3cnc(CF)cn3)ccc2F)C[C@@H](C(F)(F)F)OC(N)=N1] | 6 |
| 20 | 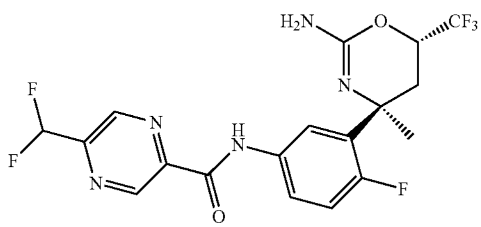 [SMILES: C[C@@]1(c2cc(NC(=O)c3cnc(C(F)F)cn3)ccc2F)C[C@@H](C(F)(F)F)OC(N)=N1] | 5 |
| 21 | 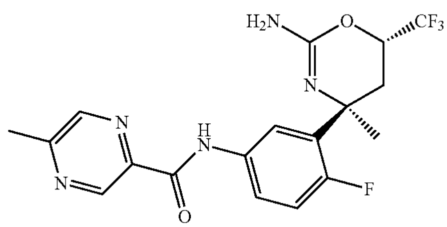 [SMILES: Cc1cnc(C(=O)Nc2ccc(F)c([C@]3(C)C[C@@H](C(F)(F)F)OC(N)=N3)c2)cn1] | 59 |
| 22 | 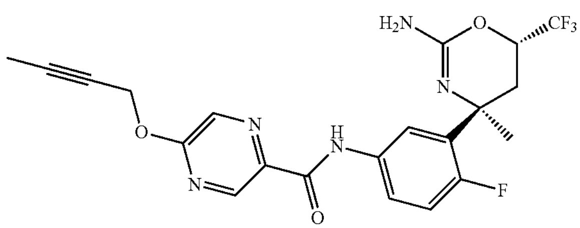 [SMILES: CC#CCOc1cnc(C(=O)Nc2ccc(F)c([C@]3(C)C[C@@H](C(F)(F)F)OC(N)=N3)c2)cn1] | 0.2 |
| 23 | 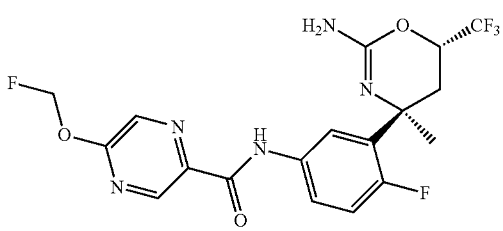 [SMILES: C[C@@]1(c2cc(NC(=O)c3cnc(OCF)cn3)ccc2F)C[C@@H](C(F)(F)F)OC(N)=N1] | 1 |
| 24 | 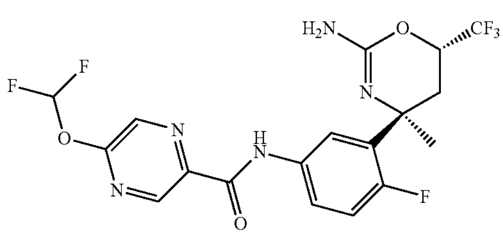 [SMILES: C[C@@]1(c2cc(NC(=O)c3cnc(OC(F)F)cn3)ccc2F)C[C@@H](C(F)(F)F)OC(N)=N1] | 3 |

TABLE 1-continued
IC$_{50}$ values of selected examples
| Exam. | Structure | BACE1 cell act. Aβ40 IC$_{50}$ [nM] |
|---|---|---|
| 25 | 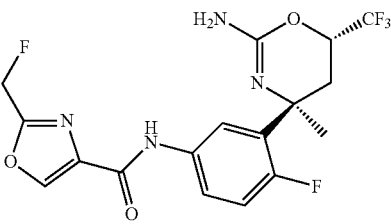 [SMILES: C[C@@]1(c2cc(NC(=O)c3coc(CF)n3)ccc2F)C[C@@H](C(F)(F)F)OC(N)=N1] | 0.8 |
| 26 | 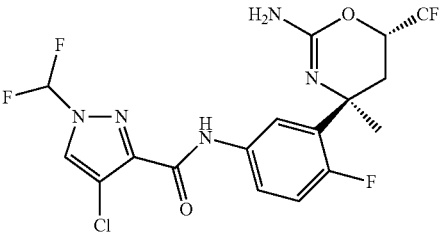 | 1 |
| 27 | 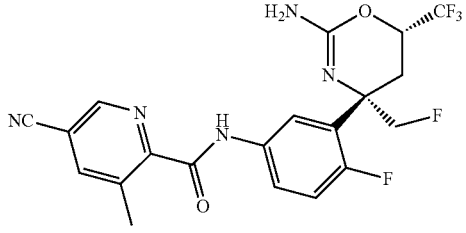 [SMILES: Cc1cc(C#N)cnc1C(=O)Nc1ccc(F)c([C@]2(CF)C[C@@H](C(F)(F)F)OC(N)=N2)c1] | 2 |
| 28 | 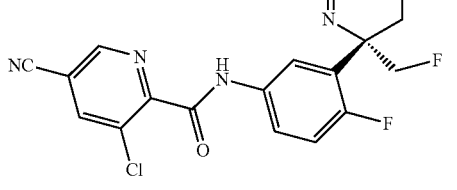 | 11 |
| 29 | 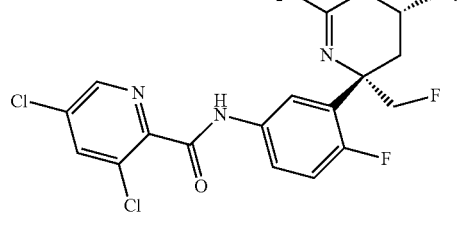 | 15 |
| 30 | 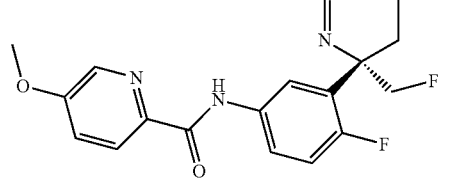 | 11 |

TABLE 1-continued

IC$_{50}$ values of selected examples

| Exam. | Structure | BACE1 cell act. Aβ40 IC$_{50}$ [nM] |
|---|---|---|
| 31 | 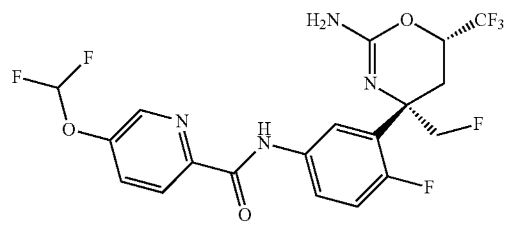 [SMILES: NC1=N[C@](CF)(c2cc(NC(=O)c3ccc(OC(F)F)cn3)ccc2F)C[C@@H](C(F)(F)F)O1] | 7 |
| 32 | 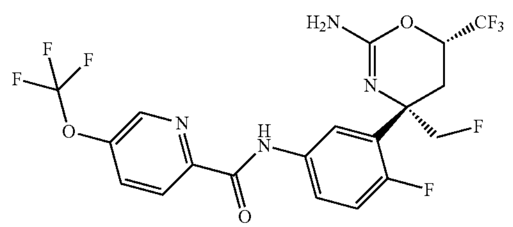 [SMILES: NC1=N[C@](CF)(c2cc(NC(=O)c3ccc(OC(F)(F)F)cn3)ccc2F)C[C@@H](C(F)(F)F)O1] | 7 |
| 33 | 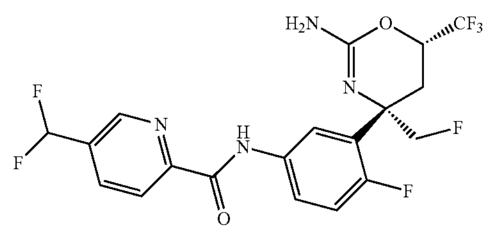 [SMILES: NC1=N[C@](CF)(c2cc(NC(=O)c3ccc(C(F)F)cn3)ccc2F)C[C@@H](C(F)(F)F)O1] | 10 |
| 34 | 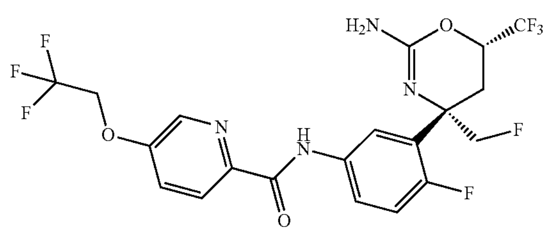 | 71 |
| 35 | 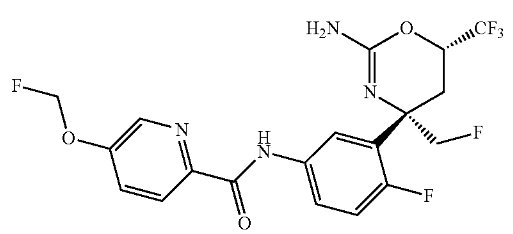 [SMILES: NC1=N[C@](CF)(c2cc(NC(=O)c3ccc(OCF)cn3)ccc2F)C[C@@H](C(F)(F)F)O1] | 19 |
| 36 | 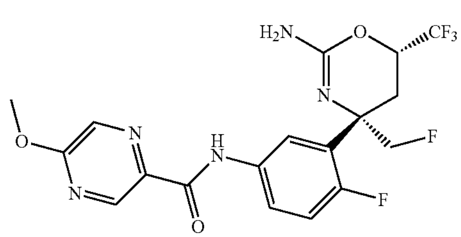 [SMILES: COc1cnc(C(=O)Nc2ccc(F)c([C@]3(CF)C[C@@H](C(F)(F)F)OC(N)=N3)c2)cn1] | 31 |

TABLE 1-continued

IC$_{50}$ values of selected examples

| Exam. | Structure | BACE1 cell act. Aβ40 IC$_{50}$ [nM] |
|---|---|---|
| 37 | 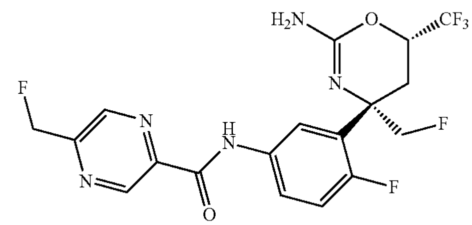 [SMILES: NC1=N[C@](CF)(c2cc(NC(=O)c3cnc(CF)cn3)ccc2F)C[C@@H](C(F)(F)F)O1] | 53 |
| 38 | 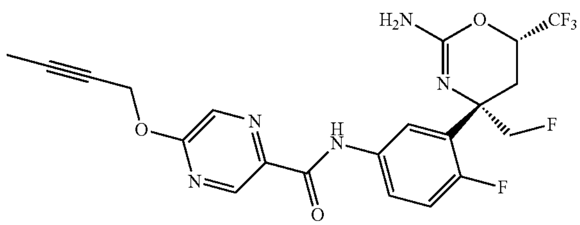 [SMILES: CC#CCOc1cnc(C(=O)Nc2ccc(F)c([C@]3(CF)C[C@@H](C(F)(F)F)OC(N)=N3)c2)cn1] | 0.6 |
| 39 | 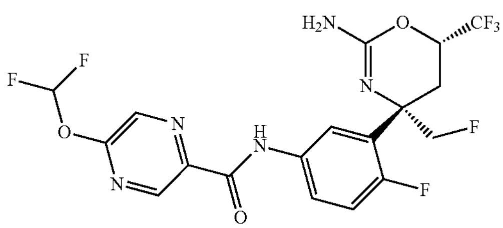 [SMILES: NC1=N[C@](CF)(c2cc(NC(=O)c3cnc(OC(F)F)cn3)ccc2F)C[C@@H](C(F)(F)F)O1] | 0.4 |
| 40 | 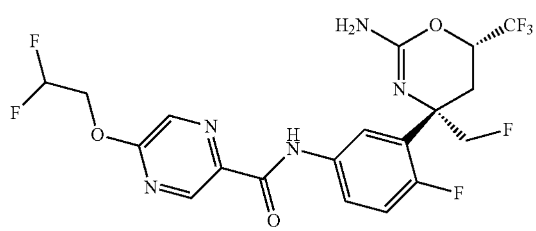 [SMILES: NC1=N[C@](CF)(c2cc(NC(=O)c3cnc(OCC(F)F)cn3)ccc2F)C[C@@H](C(F)(F)F)O1] | 29 |
| 41 | 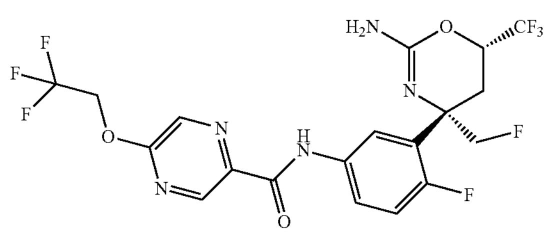 [SMILES: NC1=N[C@](CF)(c2cc(NC(=O)c3cnc(OCC(F)(F)F)cn3)ccc2F)C[C@@H](C(F)(F)F)O1] | 17 |
| 42 | 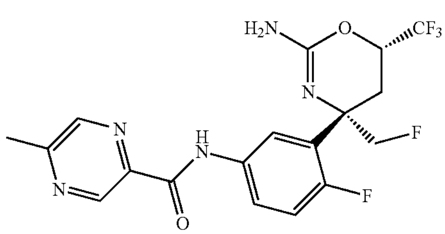 [SMILES: Cc1cnc(C(=O)Nc2ccc(F)c([C@]3(CF)C[C@@H](C(F)(F)F)OC(N)=N3)c2)cn1] | 64 |

TABLE 1-continued

IC$_{50}$ values of selected examples

| Exam. | Structure | BACE1 cell act. Aβ40 IC$_{50}$ [nM] |
|---|---|---|
| 43 | 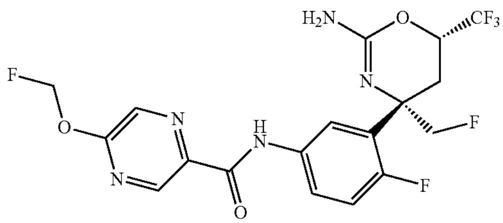 [SMILES: NC1=N[C@](CF)(c2cc(NC(=O)c3cnc(OCF)cn3)ccc2F)C[C@@H](C(F)(F)F)O1] | 3 |
| 44 | 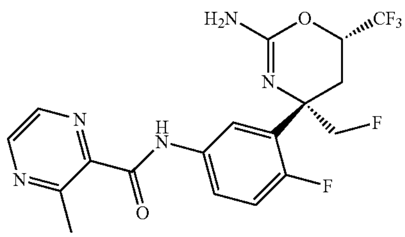 [SMILES: Cc1nccnc1C(=O)Nc1ccc(F)c([C@]2(CF)C[C@@H](C(F)(F)F)OC(N)=N2)c1] | — |
| 45 | 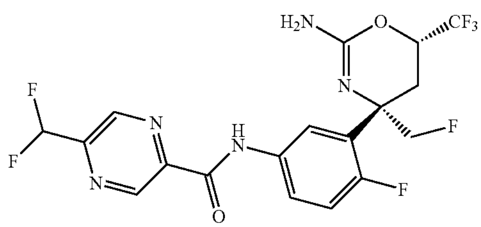 [SMILES: NC1=N[C@](CF)(c2cc(NC(=O)c3cnc(C(F)F)cn3)ccc2F)C[C@@H](C(F)(F)F)O1] | 39 |
| 46 | 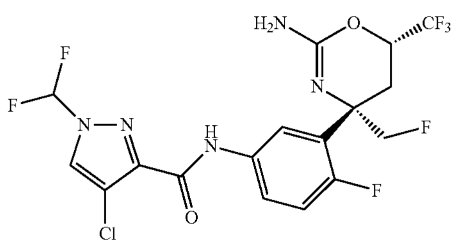 [SMILES: NC1=N[C@](CF)(c2cc(NC(=O)c3nn(C(F)F)cc3Cl)ccc2F)C[C@@H](C(F)(F)F)O1] | 3 |
| 47 | 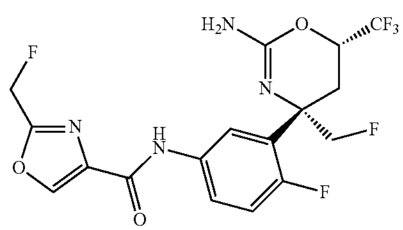 [SMILES: NC1=N[C@](CF)(c2cc(NC(=O)c3coc(CF)n3)ccc2F)C[C@@H](C(F)(F)F)O1] | 1 |
| 48 | 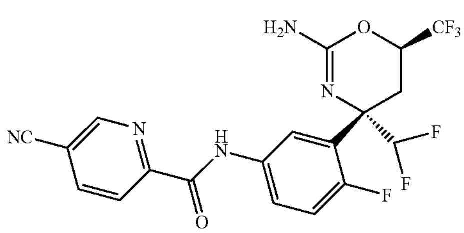 [SMILES: N#Cc1ccc(C(=O)Nc2ccc(F)c([C@]3(C(F)F)C[C@H](C(F)(F)F)OC(N)=N3)c2)nc1] | 520 |

TABLE 1-continued

IC$_{50}$ values of selected examples

| Exam. | Structure | BACE1 cell act. Aβ40 IC$_{50}$ [nM] |
|---|---|---|
| 49 | (structure: H$_2$N-substituted oxazine with CF$_3$ and CHF$_2$ groups, linked via amide to 5-cyanopyridine and difluorophenyl) | 82 |

Biological DATA

P-gp (P-Glycoprotein) Assay

Cell Lines and Vesicles Used for Transport Experiments

The LLC-PK1 cell line (ATCC #CL-101) is a porcine kidney epithelial cell line. The MDR1 (human multidrug resistance protein 1) transfected cell lines were obtained from Dr. A. Schinkel, The Netherlands Cancer Institute (Amsterdam, The Netherlands). All cell lines were cultured on permeable inserts (Costar, 0.33 cm² area, pore size 3.0 µm, low density) at 4.5·10⁵ cells/cm². Transport measurements were performed at day 4 after seeding. Tightness of the cell monolayer was controlled via the permeability of the extracellular marker lucifer yellow (10 µM). Experiments showing lucifer yellow permeation superior to 1% h were rejected.

In Vitro Transport Experiments

Bidirectional transcellular transport using LLC-PK1 and L-MDR1 LLC-PK1 cells exogenously expressing the human MDR1)

The method used for transport experiments were performed on a TECAN automated liquid handling system. Briefly, medium was removed from all compartments and the medium of receiver side was replaced with culture medium. The trans-cellular transport measurements were initiated by adding the substrate together with extracellular marker lucifer yellow to the donor side. Inhibitors were added to both sides (1 µM elacridar). Transport experiments were performed both in the basolateral-to-apical and apical-to-basolateral directions with 3 wells each. The plates were incubated at 37° C. and 5% CO$_2$ in a Liconic incubator. Samples were taken from the donor and the opposite (acceptor) side after 2 hours incubation. Concentrations of substrate in both compartments were determined by scintillation counting (digoxin) or by LC-MS/MS. The extracellular marker (lucifer yellow) was quantified using a spectrafluor plus reader at 430/535 nm (Ex/Em). In each experiment 3 different inserts were used for each condition and a mean was calculated.

Data Analysis

Bidirectional transcellular transport using LLC-PK1 and L-MDR1 cells

For the transcellular transport, the following equation was used for data evaluation:

$$P_{app} = \frac{1}{A * C_0} * \frac{dQ}{dt}$$

Where $P_{app}$, A, $C_0$, and dQ/dt represent the apparent permeability, the filter surface area, the initial concentration, and the amount transported per time period, respectively. $P_{app}$ values were calculated on the basis of a single time point (2 h).

Transport efflux ratios (ER) were calculated as follows:

$$ER = \frac{P_{app}BA}{P_{app}AB}$$

Where $P_{app}BA$ is the permeability value in the basolateral-to-apical direction, and $P_{app}AB$ the permeability value in the apical-to-basolateral direction. $P_{app}$ were not corrected for flux of the extracellular marker lucifer yellow, which was used to assess the quality of the cell mono layers.

Detection of Glutathione Conjugates (GSH)

The assay conditions for the detection of glutathione conjugates follow the procedure described by C. M. Dieckhaus et al. in Chem. Res. Toxicol. 2005, 18, 630-63.

hERG Current Measurement

The hERG current measurement was performed at an automated patch clamp system following the procedure described in R. E. Martin et al. in Bio org. Med. Chem. Lett 19 (2009), 6106-6113.

In Vivo Experiments. Inhibition of Aβ40 in Brain of Wild-Type Mice.

Female C57Bl/6J mice were treated with different doses of the compounds, 3-4 animals per treatment group. The test compound was dissolved in 5% EtOH, 10% Solutol and was applied per os at 10 ml/kg. After 4 h the animals were sacrificed and brain and plasma were collected. The brain was cut into halves and immediately frozen on dry ice. Brain was used for measurement of Aβ40 and plasma was used for determination of compound exposure. The method for Aβ40 determination in brain lysates followed the known procedure (Lanz, T. A.; Schachter, J. B. Demonstration of a common artifact in immunosorbent assays of brain extracts: Development of a solid-phase extraction protocol to enable measurement of amyloid-beta from wild-type rodent brain. J. Neurosci. Methods 2006, 157, 71-81). Brain tissue was homogenized in 2% DEA buffer in a Roche MagnaLyser (20", 4000 rpm) and subsequently centrifuged for 1 h at 100'000 g. DEA was reduced to 0.2% in 50 mM NaCl and one half of the DEA lysate was passed over an Oasis Solid Phase extraction plate (Waters; Cat.Nr. 186000679) which had been activated with MeOH and equilibrated in dH$_2$O (1 ml each). After washes in 10% and 30% MeOH (1 ml each) the Aβ-peptides were eluted in 0.8 ml 2% NH$_4$OH in 90% MeOH. The eluate was dried over a N$_2$ flow and the dried sample was reconstituted in 30 µl AlphaLISA assay buffer. Aβ40 was determined by an AlphaLISA assay (Perkin Elmer). In a white 96well half-area microplate (Perkin Elmer Cat.Nr. 6005561), 20 µl of the reconstituted sample were mixed with 5 µl biotinylated BAP-24 (specific for C-terminus of Aβ40 (Brockhaus, M.; Grunberg, J.; Rohrig, S.; Loetscher, H.; Wittenburg, N.; Baumeister, R.; Jacobsen, H.; Haass, C. Caspase-mediated cleavage is not required for the activity of presenilins in amyloidogenesis and NOTCH signaling. *Neuroreport* 1998, 9, 1481-6), stock=4.4 mg/ml, f.c.5.5 µg/ml) and 5 µl 252Q6 acceptor beads (252Q6 antibody, Invitrogen AMB0062) had been previously conjugated with AlphaLISA Acceptor beads (Perkin Elmer Cat.Nr.6772002); final dilution 1:500). The mix was incubated for 1 h at RT in the dark. Then 20 µl Streptavin-coated Donor Beads (Perkin Elmer Cat. Nr. 6760002, final dilution 1:125) were added and this final mix was incubated in the dark for another 30 min at r.t. before RFU was measured in an AlphaScreen Reader(Perkin Elmer Envision 2104).

Cathepsin D and Cathepsin E Fluorescent Substrate Kinetic Assays
General Assay Principle The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non binding surface plates from Corning) in a final volume of 51 µl. The test compounds were serially diluted in DMSO (15 concentrations, 1/3 dilution steps) and 1 µl of diluted compounds were mixed for 10 min with 40 µl of cathepsin D (from human liver, Calbiochem) diluted in assay buffer (100 mM sodium acetate, 0.05% BSA, pH 5.5; final concentration: 200 nM) or with 40 µl of recombinant human cathepsin E (R&D Systems) diluted in assay buffer (100 mM sodium acetate, 0.05% BSA, pH 4.5; final concentration: 0.01 nM). After addition of 10 µl of the cathepsin D substrate WTSVLMAAPC-MR121 diluted in cathepsin D assay buffer (final concentration: 300 nM) or 10 µl of the cathepsin E substrate MR121-CKLVF-FAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission: 695 nm) for at least 30 minutes in a kinetic measurement detecting an increase of MR121 fluorescence during the reaction time. The slope in the linear range of the kinetic was calculated and the $IC_{50}$ of the test compounds were determined using a four parameter equation for curve fitting.

CYP Inhibition Assay

Inhibition of cytochromes P450 (CYPs) 2C9, 2D6 and 3A4 was assessed using human liver microsomes and CYP-selective substrate metabolism reactions. 50 µl incubations were made up containing (finally) 0.2 mg/ml pooled human liver microsomes, 5 µM substrate (diclofenac for CYP2C9 [4'hydroxylase], dextromethorphan for CYP2D6 [O-demethylase] or midazolam for CYP3A4 [1'hydroxylase], 0.25 µL DMSO containing test inhibitor and NADPH regenerating system. Test inhibitor concentrations of 50, 16.7, 5.6, 1.9, 0.6 and 0.2 µM were assessed in singlicate. Incubations were prewarmed to 37° C. for 10 minutes before initiation by addition of NADPH regenerating system. Incubations were quenched after 5 minutes (20 minutes for dextromethorphan) by addition of 50 µl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a RapidFire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and $IC_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities, R. L. Walsky and R. S. Obach, Drug Metabolism and Disposition 32: 647-660, 2004. and S. Fowler and H. Zhang, The AAPS Journal, Vol. 10, No. 2, 410-424, 2008).

Results

TABLE 2

Biological data of selected examples

| Ex. | P-gp [1] human | GSH [2] human | hERG [3] | in vivo effect [4] | Cathepsin E $IC_{50}$ [µM] | Cathepsin D $IC_{50}$ [µM] | CYP $IC_{50}$ [µM] 3A4 | 2D6 | 2C9 |
|---|---|---|---|---|---|---|---|---|---|
| 1 | 1.90 | NF | 75 | 95 | >200 | >200 | >50 | 28 | >50 |
| 2 | 1.82 | NF | 84 | 93 | >200 | >200 | >50 | 3.9 | >50 |
| 3 | 1.61 | NF | 39 | 88 | >200 | >200 | >50 | >50 | >50 |
| 11 | 2.30 | NF | 26 | 87 | >200 | >200 | >50 | 1.6 | >50 |
| 22 | 2.63 | NF | — | 83 | >200 | 178.69 | >50 | 13.0 | 33.0 |
| 35 | 1.50 | NF | 26 | 74 | >200 | >200 | >50 | 5.2 | 33 |
| 36 | 0.71 | NF | 7 | 88 | >200 | >200 | >50 | 16.0 | >50 |
| 46 | 1.23 | NF | 8 | 61 | >200 | >200 | >50 | 24.0 | >50 |

[1] Efflux ratio
[2] NF = in vitro no adduct formation relative to control
[3] Inhibition @ 10 µM
[4] Percentage of control @ 10 mg/kg p.o

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

EXAMPLE A

Tablets of the following composition are manufactured in the usual manner:

TABLE 3 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 4 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 5 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 6

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 7

| possible suppository composition | |
|---|---|
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 8

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 9

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Abbreviations:

AcOEt, ethyl acetate; DCM, dichloromethane; DIBAH, diisobutylaluminiumhydride; EtOH, ethanol; i-PrOH, 2-propanol; MeOH, methanol; r.t., room temperature; TBME, tert-butylmethylether; TEA, triethylamine; THF, tetrahydrofuran; $T_3P®$ (2,4,6-tripropyl-1,3,5,2,4,6-trioxatriphosphorinane-2,4,6-trioxide)

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Synthesis of the Intermediate Ester II

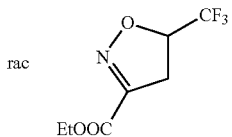 [SMILES: CCOC(=O)C1=NOC(C(F)(F)F)C1]

To a suspension of 3,3,3-trifluoroprop-1-ene (ca. 4.3 g, 45 mmol) in AcOEt (30 ml) and sodium bicarbonate (6.3 g, 75.0 mmol) was added at −78° C. a solution of (Z)-ethyl 2-chloro-2-(hydroxyimino)acetate (2.81 g, 18.0 mmol) in AcOEt (6 ml), the suspension was allowed to warm to 22° C. and stirring was continued for 60 h. The suspension was filtered, the filtrate was evaporated and the residue purified by chromatography on silica gel using heptane/AcOEt (10:1) to give ethyl 5-(trifluoromethyl)-4,5-dihydroisoxazole-3-carboxylate (3.2 g) as a colorless oil. MS: m/z=211 $[M]^+$.

Synthesis of the Intermediate Alcohol III

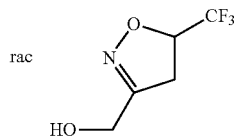 [SMILES: OCC1=NOC(C(F)(F)F)C1]

To a solution of ethyl 5-(trifluoromethyl)-4,5-dihydroisoxazole-3-carboxylate (1.0 g, 4.74 mmol) in EtOH (10 ml) was slowly added at 0° C. sodium borohydride (197 mg, 5.21 mmol) and the suspension was stirred at 0° C. for 4 h. The suspension was treated with half saturated aqueous NH4Cl, stirring was continued for 10 minutes, the mixture was extracted with diethylether, the organic layers were dried and evaporated (70 mbar/40° C.) to give crude (5-(trifluoromethyl)-4,5-dihydroisoxazol-3-yl)methanol (803 mg) as a colorless oil which was used without further purification. MS: m/z=169 [M]+.

Synthesis of the Intermediate Fluoro-Dihydroisoxazole IV

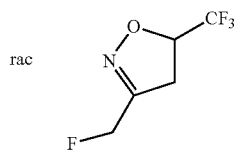 [SMILES: FCC1=NOC(C(F)(F)F)C1]

To a solution of crude (5-(trifluoromethyl)-4,5-dihydroisoxazol-3-yl)methanol (7.0 g, 41.4 mmol) in dichloromethane (140 ml) was added at −78° C. morpholinosulfur trifluoride (7.98 g, 45.5 mmol) and stirring was continued at −78° C. for 15 min, at 0° C. for 1 h and at 22° C. for 30 min. The solution was treated with cold aqueous NaHCO3, the organic layer was dried, evaporated (70 mbar/40° C.) and the residue was distilled from bulb to bulb at 100° C./0.8 mbar to give 3-(fluoromethyl)-5-(trifluoromethyl)-4,5-dihydroisoxazole (2.54 g) as a pale yellow liquid. MS: m/z=171 [M]+.

Synthesis of the Intermediate Dihydroisoxazole IV

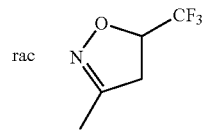

To a solution of 3,3,3-trifluoroprop-1-ene (ca. 18 g) in diethyl ether (120 ml) was added subsequently at −78° C. nitroethane (5.74 g, 76.5 mmol), TEA (76 mg, 0.75 mmol) and phenyl isocyanate (18.2 g, 153 mmol), the solution was warmed to 22° C. and stirring was continued for 60 h. The suspension was filtered and the filtrate distilled from bulb to bulb at 75° C./1.0 mbar to give 3-methyl-5-(trifluoromethyl)-4,5-dihydroisoxazole (4.69 g) as a pale yellow liquid. MS: m/z=153 [M]+.

General Procedure A: Synthesis of the Intermediate Isoxazolidines VI and VII

To a stirred solution of the arylbromide V (8.26 mmol) in THF (5 ml) and toluene (15 ml) was added at −78° C. n-BuLi (1.6 M in hexane, 4.9 ml) over 10 min and stirring was continued at −78° C. for 1 h. To a solution of the dihydroisoxazole IV (3.9 mmol) in toluene (35 ml) was added at −78° C. BF3.Et2O (7.9 mmol) which was followed by the addition of the phenyllithium reagent prepared above using an insulated cannula over 10 min keeping the temperature below −70° C. The mixture was stirred at −78° C. for 1 h, quenched with saturated aqueous NH4Cl and extracted with AcOEt. The organic layer was washed with brine, dried, evaporated and the residue was chromatographed on silica gel using a mixture of cyclohexane and AcOEt to afford the pure isoxazolidine VI.

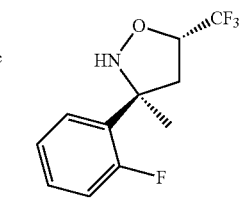

Intermediate VI-1: Starting from 3-methyl-5-(trifluoromethyl)-4,5-dihydroisoxazole, the product (3S,5S)-rel-3-(2-fluoro-phenyl)-3-methyl-5-trifluoromethyl-isoxazolidine was obtained as a pale yellow liquid. MS: m/z=250.4 [M+H]+.

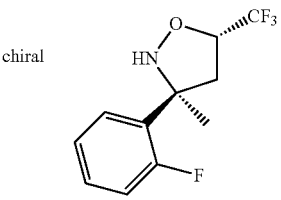 [SMILES: C[C@@]1(c2ccccc2F)C[C@@H](C(F)(F)F)ON1]

Intermediate VII-1: (3S,5S)-rel-3-(2-fluoro-phenyl)-3-methyl-5-trifluoromethyl-isoxazolidine was resolved on a chiral HPLC column (Chiralpack AD) using n-heptane/EtOH (95:5) to give the desired (3S,5S)-3-(2-fluoro-phenyl)-3-methyl-5-trifluoromethyl-isoxazolidine as the slower eluting enantiomer with positive optical rotation and (3R,5R)-3-(2-fluoro-phenyl)-3-methyl-5-trifluoromethyl-isoxazolidine as the faster eluting enantiomer with negative optical rotation.

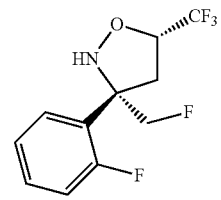

Intermediate VI-2: Starting from 3-(fluoromethyl)-5-(trifluoromethyl)-4,5-dihydroisoxazole, the product (3S,5S)-rel-3-(fluoromethyl)-3-(2-fluorophenyl)-5-(trifluoromethyl) isoxazolidine was obtained as a pale yellow liquid. MS: m/z=268.4 [M+H]+.

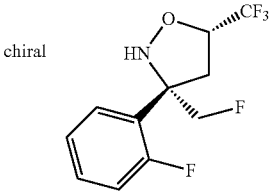 [SMILES: FC[C@@]1(c2ccccc2F)C[C@@H](C(F)(F)F)ON1]

Intermediate VII-2: (3S,5S)-rel-3-(fluoromethyl)-3-(2-fluorophenyl)-5-(trifluoromethyl)isoxazolidine was resolved on a chiral column (Reprosil NR) using n-heptane/i-PrOH (98:2) to give the desired (3S,5S)-3-fluoromethyl-3-(2-fluoro-phenyl)-5-trifluoromethyl-isoxazolidine as the slower eluting desired enantiomer with positive optical rotation and (3R,5R)-3-fluoromethyl-3-(2-fluoro-phenyl)-5-trifluoromethyl-isoxazolidine as the faster eluting enantiomer with negative optical rotation.

General Procedure B: Synthesis of the Intermediate Aminoalcohol VIII

To a solution of the isoxazolidine VII (6.4 mmol) in EtOH (40 ml) was added Pd/C (10%, 288 mg) and ammonium formate (3.2 g) and stirring of the mixture was continued at 22° C. for 5 h. The suspension was filtered, the filtrate evaporated and the residue was partitioned between AcOEt and saturated aqueous NaHCO3 solution. The organic layer was dried and evaporated to give the crude aminoalcohol VIII which was used without further purification.

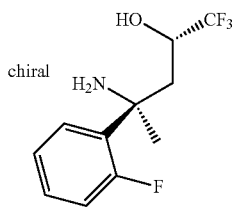 [SMILES: C[C@](N)(C[C@H](O)C(F)(F)F)c1ccccc1F]

Intermediate VIII-1: Starting from (3S,5S)-3-(2-fluoro-phenyl)-3-methyl-5-trifluoromethyl-isoxazolidine, the product (2S,4S)-4-amino-1,1,1-trifluoro-4-(2-fluorophenyl)pentan-2-ol was obtained as a colorless solid. MS: m/z=252.2 [M+H]$^+$.

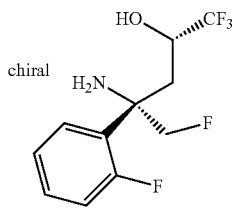 [SMILES: N[C@@](CF)(C[C@H](O)C(F)(F)F)c1ccccc1F]

Intermediate VIII-2: Starting from (3S,5S)-3-fluoromethyl-3-(2-fluoro-phenyl)-5-trifluoromethyl-isoxazolidine, the product (2S,4S)-4-amino-1,1,1,5-tetrafluoro-4-(2-fluorophenyl)pentan-2-ol was obtained as a colorless solid. MS: m/z=270.4 [M+H]$^+$.

General Procedure C: Synthesis of the Intermediate Oxazine IX

To a solution of the aminoalcohol VIII (7.3 mmol) in EtOH (38 ml) was added a solution of cyanogen bromide (5M in CH$_3$CN, 11 mmol) and the mixture was stirred in a sealed tube at 85° C. for 15 h. The mixture was evaporated and the residue partitioned between AcOEt and saturated aqueous Na$_2$CO$_3$ solution, the organic layer was dried, evaporated and the residue was purified by chromatography (Si—NH$_2$) using a mixture of heptane/AcOEt 5:1 to 0:1) to afford the pure oxazine IX.

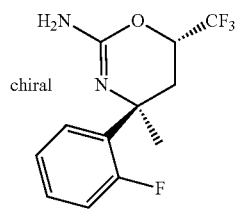 [SMILES: C[C@@]1(c2ccccc2F)C[C@@H](C(F)(F)F)OC(N)=N1]

Intermediate IX-1: Starting from (2S,4S)-4-amino-1,1,1-trifluoro-4-(2-fluorophenyl)pentan-2-ol, the product (4S,6S)-4-(2-fluorophenyl)-4-methyl-6-(trifluoromethyl)-5,6-dihydro-4H-1,3-oxazin-2-amine was obtained as a colorless oil. MS: m/z=277.1 [M+H]$^+$.

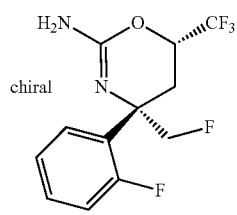 [SMILES: NC1=N[C@](CF)(c2ccccc2F)C[C@@H](C(F)(F)F)O1]

Intermediate IX-2: Starting from (2S,4S)-4-amino-1,1,1,5-tetrafluoro-4-(2-fluorophenyl)pentan-2-ol, the product (4S,6S)-4-(fluoromethyl)-4-(2-fluorophenyl)-6-(trifluoromethyl)-5,6-dihydro-4H-1,3-oxazin-2-amine was obtained as a colorless oil. MS: m/z=295.4 [M+H]$^+$.

General Procedure D: Synthesis of the Intermediate Nitro-Oxazine X

To concentrated sulfuric acid (13 ml) was added portionwise the oxazine IX (3.0 mmol) at 22° C., the solution obtained was cooled to 0° C. and treated with red fuming HNO$_3$ (0.19 ml) over 20 min and stirring was continued at 0° C. for 1 h. The reaction mixture was slowly added to crushed ice (60 g), the pH was adjusted to 10 using NaOH, the aqueous layer was extracted with AcOEt, the organic layer was dried, evaporated and the residue was chromatographed on silica gel using a mixture of heptane/AcOEt 3:1 to afford the pure nitro-oxazine X.

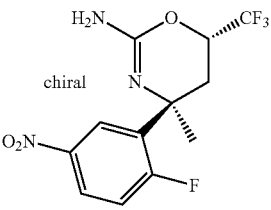 [SMILES: C[C@@]1(c2cc([N+](=O)[O-])ccc2F)C[C@@H](C(F)(F)F)OC(N)=N1]

Intermediate X-1: Starting from (4S,6S)-4-(2-fluorophenyl)-4-methyl-6-(trifluoromethyl)-5,6-dihydro-4H-1,3-oxazin-2-amine, the product (4S,6S)-4-(2-fluoro-5-nitrophenyl)-4-methyl-6-(trifluoromethyl)-5,6-dihydro-4H-1,3-oxazin-2-amine was obtained as a pale yellow oil. MS: m/z=322.5 [M+H]$^+$.

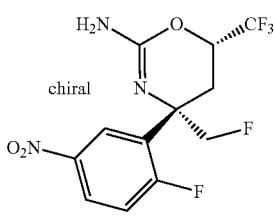

Intermediate X-2: Starting from (4S,6S)-4-(fluoromethyl)-4-(2-fluorophenyl)-6-(trifluoromethyl)-5,6-dihydro-4H-1,3-oxazin-2-amine, the product (4S,6S)-4-(2-fluoro-5-nitrophenyl)-4-(fluoromethyl)-6-(trifluoromethyl)-5,6-dihydro-4H-1,3-oxazin-2-amine was obtained as a colorless foam. MS: m/z=340.4 [M+H]$^+$.

General Procedure E: Synthesis of the Intermediate Aniline XI

A suspension of the nitro-oxazine X (2.6 mmol) in EtOH (40 ml) and TEA (0.2 ml) was treated with Pd/C (10%, 80 mg) and the mixture was hydrogenated at atmospheric pressure and 22° C. for 2 h. The mixture was filtered, the filtrated evaporated and the residue containing crude aniline XI was used without further purification.

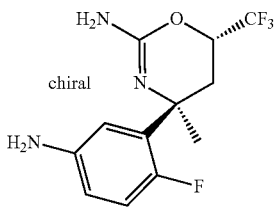

Intermediate XI-1: Starting from (4S,6S)-4-(2-fluoro-5-nitrophenyl)-4-methyl-6-(trifluoromethyl)-5,6-dihydro-4H-1,3-oxazin-2-amine, the product (4S,6S)-4-(5-amino-2-fluorophenyl)-4-methyl-6-(trifluoromethyl)-5,6-dihydro-4H-1,3-oxazin-2-amine was obtained as a colorless foam. MS: m/z=292.5 [M+H]$^+$.

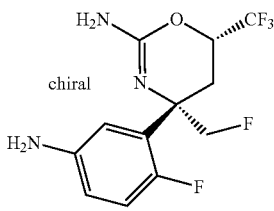 [SMILES: NC1=N[C@](CF)(c2cc(N)ccc2F)C[C@@H](C(F)(F)F)O1]

Intermediate XI-2: Starting from (4S,6S)-4-(2-fluoro-5-nitrophenyl)-4-(fluoromethyl)-6-(trifluoromethyl)-5,6-dihydro-4H-1,3-oxazin-2-amine, the product (4S,6S)-4-(5-amino-2-fluorophenyl)-4-(fluoromethyl)-6-(trifluoromethyl)-5,6-dihydro-4H-1,3-oxazin-2-amine was obtained as a colorless solid. MS: m/z=310.4 [M+H]$^+$.

Synthesis of the Intermediate Sulfinyl Imine XIV-1

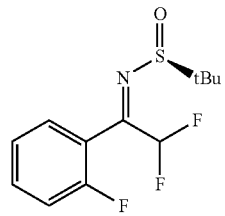 [SMILES: CC(C)(C)[S@](=O)/N=C(/c1ccccc1F)C(F)F]

Under an inert atmosphere the light yellow solution of 2,2-difluoro-1-(2-fluorophenyl)ethanone (8.0 g, 45.9 mmol) in THF (280 ml) was treated at r.t. with (S)-2-methylpropane-2-sulfinamide (5.68 g, 45.9 mmol) followed by titanium(IV) ethoxide (21.0 g, 19.3 ml, 91.9 mmol). The light yellow solution was heated to reflux and stirred for 2 hours. The reaction mixture was cooled to r.t., poured into half-saturated brine, diluted with AcOEt (100 ml) and stirred vigorously for 1 hour. After filtration through a layer of Dicalite® and washing with AcOEt the aqueous layer was separated and extracted with AcOEt (2×150 ml). The organic layers were dried over MgSO$_4$ and evaporated at reduced pressure. The crude product was purified by flash chromatography on silica gel (eluent: heptane/AcOEt 10:1) to give (S,Z)—N-(2,2-difluoro-1-(2-fluorophenyl)ethylidene)-2-methylpropane-2-sulfinamide (8.27 g, 64.9% yield) as a yellow oil. MS: m/z=278.0 [M+H]$^+$.

The 2,2-difluoro-1-(2-fluoro-phenyl)-ethanone was obtained as follows:

In a dry flask a suspension of magnesium (1.26 g, 52.0 mmol) in THF (100 ml) was treated at r.t. under an inert atmosphere with chloro-trimethyl silane (11.3 g, 13.3 ml, 104 mmol). The suspension was cooled to 0° C. and 2,2,2-trifluoro-1-(2-fluorophenyl)ethanone (4.99 g, 26 mmol) was added dropwise within 4 min while the internal temperature rose to 13° C. After complete addition the internal temperature has reached 20° C. Thereafter the suspension was cooled to 0° C. and stirred for 1 hour. For the workup, the yellow solution was allowed to warm to r.t., decanted and hydrochloric acid (37%; 20.5 g, 17.1 ml, 208 mmol) was added dropwise within 3 minutes while cooling with an ice bath. The turbid solution was stirred at r.t. for 20 min. The mixture was treated with brine (200 ml), and the aqueous layer was separated and extracted twice with AcOEt. The organic layers were washed with a saturated solution of NaHCO$_3$ and brine, then dried and evaporated to give after standing at r.t. the 2,2-difluoro-1-(2-fluorophenyl)ethanone (4.292 g, 94.8% yield) as a light yellow semisolid. MS: m/z=174 [M]$^+$.

Synthesis of the Intermediate Sulfinamide Esters XV-1 and XV-2

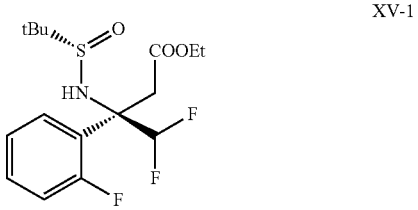

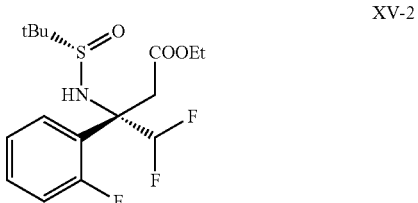

In a dry flask under an inert atmosphere copper(I) chloride (2.74 g, 27.7 mmol) and activated zinc powder (14.5 g, 221 mmol) were mixed and heated to 130° C. After cooling to r.t. dry THF (80 ml) was added and under stirring the dispersion was heated to reflux for 30 min. The external heating was removed and a solution of ethyl 2-bromoacetate (11.5 g, 7.65 ml, 69.1 mmol) in dry THF (40 ml) was added dropwise in a manner that the temperature was maintained at 55° C. After complete addition stirring at 55° C. was continued for 30 min. Thereafter, the mixture was cooled to 5° C. and a solution of the (S,Z)—N-(2,2-difluoro-1-(2-fluorophenyl)ethylidene)-2-methylpropane-2-sulfinamide (7.67 g, 27.7 mmol) in dry THF (40 ml) was added dropwise within 10 min while the temperature was kept below 5° C. In order to complete the reaction stirring was continued at 0° C. for 1 h. For the workup, the reaction mixture was filtered through a layer of Dicalite® which was washed with TBME. The filtrate was extracted with a saturated solution of $NH_4Cl$, the organic layer was dried over $MgSO_4$ and evaporated at reduced pressure. The crude product was purified by 2 consecutive chromatographies on silica gel (eluent: heptane/AcOEt 4:1, then 3:1 for the mixture of isomers) to give the (R)-ethyl 3-((S)-1,1-dimethylethylsulfinamido)-4,4-difluoro-3-(2-fluorophenyl)butanoate (XV-1) (yellow oil, 5.17 g, 51.2% yield) as the first eluting isomer and the (S)-ethyl 3-((S)-1,1-dimethylethylsulfinamido)-4,4-difluoro-3-(2-fluorophenyl)butanoate (XV-2) (orange solid, 2.59 g, 25.7% yield) as the second eluting isomer.

Synthesis of the Intermediate Aldehydes XVI

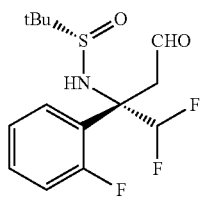

XVI-1

Intermediate XVI-1: In a dry flask under an inert atmosphere the light yellow solution of (S)-ethyl 3-((S)-1,1-dimethylethylsulfinamido)-4,4-difluoro-3-(2-fluorophenyl)butanoate (XV-2) (2.59 g, 7.09 mmol) in DCM (75 ml) was treated dropwise with DIBAH (1 M in toluene; 10.6 ml, 10.6 mmol) keeping the internal temperature below −72° C. After complete addition the reaction mixture was stirred at −78° C. for 30 min. For the workup, the mixture was quenched with a saturated solution of $NH_4Cl$ (10 ml), left to warm to room temperature and stirred for 30 min. The thick suspension was filtered through a layer of Dicalite® which was washed twice with DCM. The filtrate was treated with a half-saturated solution of $NH_4Cl$ and extracted three times with DCM. The combined organic layers were dried over $MgSO_4$ and evaporated. The crude product was purified by chromatography on silica gel (eluent: heptane/AcOEt; gradient: 30-50% AcOEt) to yield the (S)—N—((S)-1,1-difluoro-2-(2-fluorophenyl)-4-oxobutan-2-yl)-2-methylpropane-2-sulfinamide (XVI-1) (704 mg, 31% yield) as a light yellow oil and the starting ester XV-2 (1.28 g, 49% yield) as a colorless oil. MS: m/z=322.4 $(M+H)^+$.

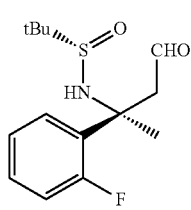

XVI-2

Intermediate XVI-2: Starting from (S)-ethyl 3-((R)-1,1-dimethylethylsulfinamido)-3-(2-fluorophenyl)butanoate [H. Hilpert et al. US20120225858 (2012)] and following the procedure for the synthesis of intermediate XVI-1, the product (R)—N—((S)-2-(2-fluorophenyl)-4-oxobutan-2-yl)-2-methylpropane-2-sulfinamide (XVI-2) was obtained as a light yellow oil (46.5% yield). MS: m/z=286.5 $(M+H)^+$.

Synthesis of the Intermediate Alcohols XVII and XVII

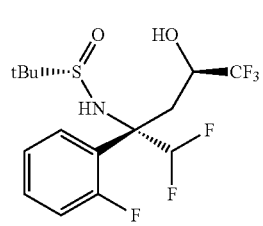

XVII-1

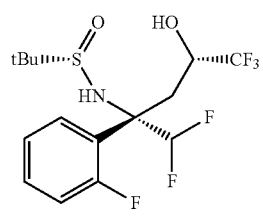

XVII-2

Intermediates XVII-1 and XVII-2: In a dry flask under an inert atmosphere a solution of (S)—N—((S)-1,1-difluoro-2-(2-fluorophenyl)-4-oxobutan-2-yl)-2-methylpropane-2-sulfinamide (XVI-1) (1.45 g, 4.51 mmol) in THF (30 ml) was treated at 0° C. with (trifluoromethyl)trimethylsilane (1.28 g, 1.33 ml, 9.02 mmol) and dropwise with TBAF (1 M in THF, dried over molecular sieves 4 Å; 0.451 ml, 0.451 mmol). The slightly exothermic addition was completed within 3 min, thereafter the reaction mixture was stirred at 0° C. for 3 h, then left to warm to r.t. and stirred overnight. For the workup, the reaction mixture was quenched with a saturated solution of $NH_4Cl$ and extracted three times with AcOEt. The organic layers were washed with brine, dried over $MgSO_4$ and evaporated at reduced pressure. The crude product was purified by chromatography on silica gel (eluent: heptane/AcOEt; gradient: 0-90% AcOEt) to yield the (S)-2-methyl-N-((2S,4R)-1,1,5,5,5-pentafluoro-2-(2-fluorophenyl)-4-hydroxypentan-2-yl)propane-2-sulfinamide (XVII-1) (yellow oil, 377 mg as an approximately 7:3-mixture with its O-trimethylsilyl derivative) as the faster eluting epimer, the (S)-2-methyl-N-((2S,4S)-1,1,5,5,5-pentafluoro-2-(2-fluorophenyl)-4-hydroxypentan-2-yl)propane-2-sulfinamide (XVII-2) (yellow solid, 209 mg, 12% yield) as the second eluting epimer [MS: m/z=392.5 $(M+H)^+$], and the starting aldehyde (yellow oil, crystallized on standing, 627 mg, 36% yield).

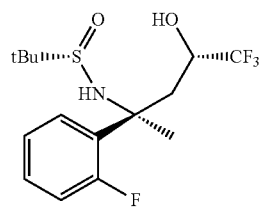

XVII-3

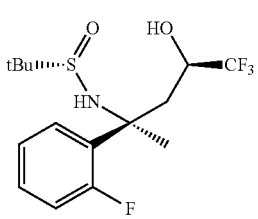

XVII-4

Intermediates XVII-3 and XVII-4: Starting from (R)—N—((S)-2-(2-fluorophenyl)-4-oxobutan-2-yl)-2-methylpropane-2-sulfinamide (XVI-2) and following the procedure for the synthesis of intermediate XVII-1 and XVII-2, the products (R)-2-methyl-N-((2S,4S)-5,5,5-trifluoro-2-(2-fluorophenyl)-4-hydroxypentan-2-yl)propane-2-sulfinamide (XVII-3) and (R)-2-methyl-N-((2S,4R)-5,5,5-trifluoro-2-(2-fluorophenyl)-4-hydroxypentan-2-yl)propane-2-sulfinamide (XVII-4) were obtained.

XVII-3: first eluting epimer as a light yellow solid (24.3% yield). MS: m/z=354.6 (M−H)⁻.

XVII-4: second eluting epimer as a light brown solid (8.5% yield). MS: m/z=356.5 (M+H)⁺.

Synthesis of the Intermediate Amino Alcohols XVIII

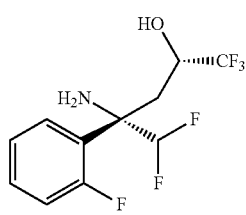

XVIII-1

Intermediate XVIII-1: Under an inert atmosphere a solution of (S)-2-methyl-N-((2S,4S)-1,1,5,5,5-pentafluoro-2-(2-fluorophenyl)-4-hydroxypentan-2-yl)propane-2-sulfinamide (XVII-2) (261 mg, 0.667 mmol) and hydrochloric acid (4 M in dioxane, 0.667 ml, 2.67 mmol) in MeOH (5 ml) was stirred at 25° C. After 4 h the solvent was removed at reduced pressure. The residue was treated with a half-saturated solution of Na₂CO₃ and extracted three times with AcOEt. The combined organic layers were dried over MgSO₄ and evaporated at reduced pressure. The crude product was purified by chromatography on silica gel (eluent: heptane/AcOEt 10:1) to yield the (2S,4S)-4-amino-1,1,1,5,5-pentafluoro-4-(2-fluorophenyl)pentan-2-ol (XVIII-1) (168 mg, 87.7%) as a light yellow solid. MS: m/z=288.5 (M+H)⁺.

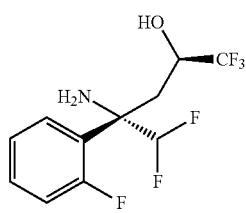

XVIII-2

Intermediate XVIII-2: Starting from the mixture of (S)-2-methyl-N-((2S,4R)-1,1,5,5,5-pentafluoro-2-(2-fluorophenyl)-4-hydroxypentan-2-yl)propane-2-sulfinamide (XVII-1) and its O-trimethylsilyl derivative and following the procedure for the synthesis of intermediate XVIII-1, the product (2R,4S)-4-amino-1,1,1,5,5-pentafluoro-4-(2-fluorophenyl)pentan-2-ol(XVIII-2) was obtained as a light yellow solid (95% yield). MS: m/z=288.5 (M+H)⁺.

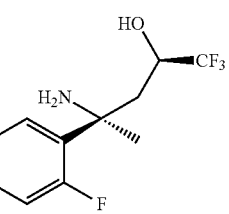

XVIII-3

Intermediate XVIII-3: Starting (R)-2-methyl-N-((2S,4R)-5,5,5-trifluoro-2-(2-fluorophenyl)-4-hydroxypentan-2-yl)propane-2-sulfinamide (XVII-4) and following the procedure for the synthesis of intermediate XVIII-1, the product (2R,4S)-4-amino-1,1,1-trifluoro-4-(2-fluorophenyl)pentan-2-ol (XVIII-3) was obtained as a light yellow solid (67.3% yield). MS: m/z =252.5 (M+H)⁺.

Synthesis of the Intermediate Oxazines XIX

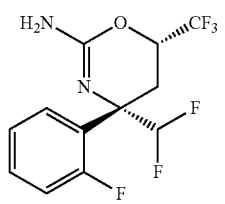

XIX-1

Intermediate XIX-1: Starting from (2S,4S)-4-amino-1,1,1,5,5-pentafluoro-4-(2-fluorophenyl)pentan-2-ol (XVIII-1) and following General Procedure C, the product (4S,6S)-4-(difluoromethyl)-4-(2-fluorophenyl)-6-(trifluoromethyl)-5,6-dihydro-4H-1,3-oxazin-2-amine (XIX-1) was obtained as a colorless solid (46.2% yield). MS: m/z=313.4 [M+H]⁺.

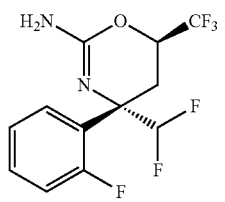

XIX-2

Intermediate XIX-2: Starting from (2R,4S)-4-amino-1,1,1,5,5-pentafluoro-4-(2-fluorophenyl)pentan-2-ol (XVIII-2) and following General Procedure C, the product (4S,6R)-4-(difluoromethyl)-4-(2-fluorophenyl)-6-(trifluoromethyl)-5,6-dihydro-4H-1,3-oxazin-2-amine (XIX-2) was obtained as a colorless oil (80.2% yield; purity approx. 60%). MS: m/z=313.4 [M+H]⁺.

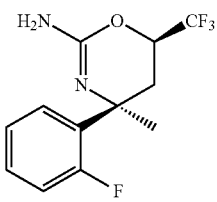

XIX-3

Intermediate XIX-3: Starting from (2R,4S)-4-amino-1,1,1-trifluoro-4-(2-fluorophenyl)pentan-2-ol (XVIII-3) and following General Procedure C, the product (4S,6R)-4-(2-fluorophenyl)-4-methyl-6-(trifluoromethyl)-5,6-dihydro-4H-1,3-oxazin-2-amine (XIX-3) was obtained as a light brown oil (60.6% yield). MS: m/z=277.5 [M+H]$^+$.

Synthesis of the Intermediate Nitro-Oxazines XX

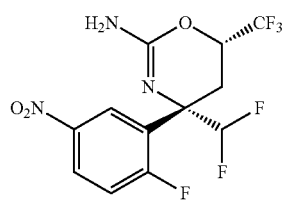

XX-1

Intermediate XX-1: Starting from (4S,6S)-4-(difluoromethyl)-4-(2-fluorophenyl)-6-(trifluoromethyl)-5,6-dihydro-4H-1,3-oxazin-2-amine (XIX-1) and following General Procedure D, the product (4S,6S)-4-(difluoromethyl)-4-(2-fluoro-5-nitrophenyl)-6-(trifluoromethyl)-5,6-dihydro-4H-1,3-oxazin-2-amine (XX-1) was obtained as a colorless solid (73.2% yield). MS: m/z=358.4 [M+H]$^+$.

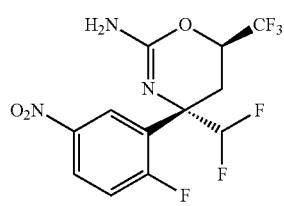

XX-2

Intermediate XX-2: Starting from (4S,6R)-4-(difluoromethyl)-4-(2-fluorophenyl)-6-(trifluoromethyl)-5,6-dihydro-4H-1,3-oxazin-2-amine (XIX-2) and following General Procedure D, the product (4S,6R)-4-(difluoromethyl)-4-(2-fluoro-5-nitrophenyl)-6-(trifluoromethyl)-5,6-dihydro-4H-1,3-oxazin-2-amine (XX-2) was obtained as a colorless foam (45.7% yield). MS: m/z=358.5 [M+H]$^+$.

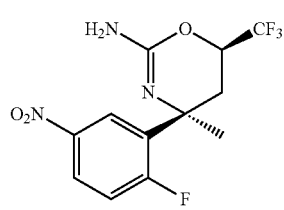

XX-3

Intermediate XX-3: Starting from (4S,6R)-4-(2-fluorophenyl)-4-methyl-6-(trifluoromethyl)-5,6-dihydro-4H-1,3-oxazin-2-amine (XIX-3) and following General Procedure D, the product (4S,6R)-4-(2-fluoro-5-nitrophenyl)-4-methyl-6-(trifluoromethyl)-5,6-dihydro-4H-1,3-oxazin-2-amine (XX-3) was obtained as a light yellow viscous oil (54% yield). MS: m/z=322.4[M+H]$^+$.

Synthesis of the Intermediate Anilines XXI

XXI-1

Intermediate XXI-1: Starting from (4S,6S)-4-(difluoromethyl)-4-(2-fluoro-5-nitrophenyl)-6-(trifluoromethyl)-5,6-dihydro-4H-1,3-oxazin-2-amine (XX-1) and following General Procedure E, the product (4S,6S)-4-(5-amino-2-fluorophenyl)-4-(difluoromethyl)-6-(trifluoromethyl)-5,6-dihydro-4H-1,3-oxazin-2-amine (XXI-1) was obtained as a colorless solid (quant. yield). MS: m/z=328.4 [M+H]$^+$.

XXI-2

Intermediate XXI-2: Starting from (4S,6R)-4-(difluoromethyl)-4-(2-fluoro-5-nitrophenyl)-6-(trifluoromethyl)-5,6-dihydro-4H-1,3-oxazin-2-amine (XX-2) and following General Procedure E, the product (4S,6R)-4-(5-amino-2-fluorophenyl)-4-(difluoromethyl)-6-(trifluoromethyl)-5,6-dihydro-4H-1,3-oxazin-2-amine (XXI-2) was obtained as a light grey foam (95.4% yield). MS: m/z=328.5 [M+H]$^+$.

XXI-3

Intermediate XXI-3: Starting from (4S,6R)-4-(2-fluoro-5-nitrophenyl)-4-methyl-6-(trifluoromethyl)-5,6-dihydro-4H-1,3-oxazin-2-amine (XX-3) and following General Procedure E, the product (4S,6R)-4-(5-amino-2-fluorophenyl)-4-methyl-6-(trifluoromethyl)-5,6-dihydro-4H-1,3-oxazin-2-amine (XXI-3) was obtained as a white solid (95.1% yield). MS: m/z=292.4 [M+H]$^+$.

General Procedure F for the Synthesis of the Final Examples I

To a solution of the acid XII (0.16 mmol) in MeOH (1 ml) was added at 22° C. 4-(4,6-dimethoxy-1,3,5-triazin-2yl)-4-methyl-morpholiniumchloride (0.19 mmol) and stirring was continued at 0° C. for 30 min. To the mixture was added a solution of the aniline XI (0.15 mmol) in MeOH (2 ml) and stirring was continued at 0° C. for 4 h. The mixture was evaporated and the residue partitioned between saturated aqueous $Na_2CO_3$ and ethyl acetate. The organic layer was dried, evaporated and the residue was purified by chromatography (Si—NH2) using a mixture of heptane ethyl acetate 1:1) to afford the final examples I.

General Procedure G for the Synthesis of the Final Examples of Formula I

Under an inert atmosphere a solution/suspension of the carboxylic acid (1.7 mmol) and the intermediate aniline XXI (1.62 mmol) in AcOEt (6.7 ml) was treated dropwise with $T_3P$® (50% in AcOEt) (2.4 mmol, 1.43 ml) while keeping the temperature at 25° C. After complete addition the reaction was stirred at 25° C. for 20 hours. For the workup, the reaction mixture was quenched with a saturated solution of $NaHCO_3$ (20 ml), the layers were separated and the aqueous phase was extracted with AcOEt (7 ml). The combined organic layers were washed with brine and dried over $Na_2SO_4$. Removal of the solvent left the crude product which was purified by chromatography on silica gel using a mixture of DCM/MeOH or heptane/AcOEt or by preparative HPLC to give the pure amides.

The following compounds were prepared following General Procedure F or G and, depending on the reaction and purification conditions, they were isolated in either the free base form or as a salt. Examples 1-7 were prepared by General Procedure F.

EXAMPLE 1

N-(3-((4S,6S)-2-amino-4-methyl-6-(trifluoromethyl)-5,6-dihydro-4H-1,3-oxazin-4-yl)-4-fluorophenyl)-5-cyanopicolinamide The coupling of (4S,6S)-4-(5-amino-2-fluorophenyl)-4-methyl-6-(trifluoromethyl)-5,6-dihydro-4H-1,3-oxazin-2-amine and 5-cyano-pyridine-2-carboxylic acid yielded the title compound as a colorless solid. MS: m/z=422.5 $[M+H]^+$.

EXAMPLE 2

N-(3-((4S,6S)-2-amino-4-methyl-6-(trifluoromethyl)-5,6-dihydro-4H-1,3-oxazin-4-yl)-4-fluorophenyl)-5-chloropicolinamide The coupling of (4S,6S)-4-(5-amino-2-fluorophenyl)-4-methyl-6-(trifluoromethyl)-5,6-dihydro-4H-1,3-oxazin-2-amine and 5-chloro-pyridine-2-carboxylic acid yielded the title compound as a colorless solid. MS: m/z=431.4 $[M+H]^+$.

EXAMPLE 3

N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide The coupling of (4S,6S)-4-(5-amino-2-fluorophenyl)-4-(fluoromethyl)-6-(trifluoromethyl)-5,6-dihydro-4H-1,3-oxazin-2-amine and 5-cyano-pyridine-2-carboxylic acid yielded the title compound as a colorless solid. MS: m/z=440.4 $[M+H]^+$.

EXAMPLE 4

N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide The coupling of (4S,6S)-4-(5-amino-2-fluorophenyl)-4-(fluoromethyl)-6-(trifluoromethyl)-5,6-dihydro-4H-1,3-oxazin-2-amine and 5-chloro-pyridine-2-carboxylic acid yielded the title compound as a colorless solid. MS: m/z=449.4 $[M+H]^+$.

EXAMPLE 5

N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide The coupling of (4S,6S)-4-(5-amino-2-fluorophenyl)-4-methyl-6-(trifluoromethyl)-5,6-dihydro-4H-1,3-oxazin-2-amine and 5-methoxy-pyrazine-2-carboxylic acid yielded the title compound as a colorless solid. MS: m/z=428.4 $[M+H]^+$.

EXAMPLE 6

N-(3-((4S,6S)-2-amino-4-methyl-6-(trifluoromethyl)-5,6-dihydro-4H-1,3-oxazin-4-yl)-4-fluorophenyl)-5-(2,2-difluoroethoxyl)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine and 5-(2,2-difluoro-ethoxy)-pyrazine-2-carboxylic acid (prepared as described in in Suzuki Y. et al., WO 2009/091 016) yielded the title compound as a colorless solid. MS: m/z=428.4 $[M+H]^+$.

EXAMPLE 7

N-(3-((4S,6S)-2-amino-4-methyl-6-(trifluoromethyl)-5,6-dihydro-4H-1,3-oxazin-4-yl)-4-fluorophenyl)-5-(2,2,2-trifluoroethoxyl)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine and 5-(2,2,2-trifluoro-ethoxy)-pyrazine-2-carboxylic acid (prepared as described in Suzuki Y. et al., WO 2009/091 016) yielded the title compound as a colorless solid. MS: m/z=496.4 $[M+H]^+$.

EXAMPLE 8

N-(3-((4S,6R)-2-Amino-4-methyl-6-(trifluoromethyl)-5,6-dihydro-4H-1,3-oxazin-4-yl)-4-fluorophenyl)-5-cyanopicolinamide The coupling of (4S,6R)-4-(5-amino-2-fluorophenyl)-4-methyl-6-(trifluoromethyl)-5,6-dihydro-4H-1,3-oxazin-2-amine (XXI-3) and 5-cyano-pyridine-2-carboxylic acid following General Procedure F yielded the title compound as a light yellow foam. MS: m/z=422.4 $[M+H]^+$.

EXAMPLE 9

N-(3-((4S,6R)-2-Amino-4-methyl-6-(trifluoromethyl)-5,6-dihydro-4H-1,3-oxazin-4-yl)-4-fluorophenyl)-5-chloropicolinamide The coupling of (4S,6R)-4-(5-amino-2-fluorophenyl)-4-methyl-6-(trifluoromethyl)-5,6-dihydro-4H-1,3-oxazin-2- amine (XXI-3) and 5-chloro-pyridine-2-carboxylic acid following General Procedure F yielded the title compound as a white foam. MS: m/z=431.4 [M+H]$^+$.

Example 10

N-(3-((4S,6S)-2-Amino-4-methyl-6-(trifluoromethyl)-5,6-dihydro-4H-1,3-oxazin-4-yl)-4-fluorophenyl)-3,5-chloropicolinamide The coupling of (4S,6S)-4-(5-amino-2-fluorophenyl)-4-methyl-6-(trifluoromethyl)-5,6-dihydro-4H-1,3-oxazin-2-amine (XI-1) and 3,5-chloro-pyridine-2-carboxylic acid following General Procedure F yielded the title compound as a colorless solid. MS: m/z=465.4 [M+H]', 467.4 [M+2+H]', 469.4 [M+4+H]$^+$.

EXAMPLE 11

N-(3-((4S,6S)-2-Amino-4-methyl-6-(trifluoromethyl)-5,6-dihydro-4H-1,3-oxazin-4-yl)-4-fluorophenyl)-5-(fluoromethoxy)picolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-(fluoromethoxy)picolinic acid [CAS 1174321-03-9; J. M. Ellard et al. WO2011009898 (2011)] following General Procedure F yielded the title compound as a colorless solid. MS: m/z=445.4 [M+H]$^+$.

EXAMPLE 12

N-(3-((4S,6S)-2-Amino-4-methyl-6-(trifluoromethyl)-5,6-dihydro-4H-1,3-oxazin-4-yl)-4-fluorophenyl)-5-cyano-3-methylpicolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-cyano-3-methylpicolinic acid [S. Badiger et al. WO2011009943 (2011)] following General Procedure G yielded the title compound as a colorless amorphous solid. MS: m/z=436.5 [M+H]$^+$.

EXAMPLE 13

N-(3-((4S,6S)-2-Amino-4-methyl-6-(trifluoromethyl)-5,6-dihydro-4H-1,3-oxazin-4-yl)-4-fluorophenyl)-3-chloro-5-cyanopicolinamide The coupling of (4S,6S)-4-(5-amino-2-fluorophenyl)-4-methyl-6-(trifluoromethyl)-5,6-dihydro-4H-1,3-oxazin-2-amine (XI-1) and 3-chloro-5-cyanopicolinic acid following General Procedure G yielded the title compound as a colorless amorphous solid. MS: m/z=456.4 [M+H]$^+$.

EXAMPLE 14

N-(3-((4S,6S)-2-Amino-4-methyl-6-(trifluoromethyl)-5,6-dihydro-4H-1,3-oxazin-4-yl)-4-fluorophenyl)-5-methoxypicolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-methoxy-picolinic acid following General Procedure G yielded the title compound as a colorless amorphous solid. MS: m/z=427.5 [M+H]$^+$.

EXAMPLE 15

N-(3-((4S,6S)-2-Amino-4-methyl-6-(trifluoromethyl)-5,6-dihydro-4H-1,3-oxazin-4-yl)-4-fluorophenyl)-5-(difluoromethoxy)picolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-(difluoromethoxy)picolinic acid [J. D. Scott et al. WO2011044181 (2011)] following General Procedure G yielded the title compound as a colorless amorphous solid. MS: m/z=463.4 [M+H]$^+$.

EXAMPLE 16

N-(3-((4S,6S)-2-Amino-4-methyl-6-(trifluoromethyl)-5,6-dihydro-4H-1,3-oxazin-4-yl)-4-fluorophenyl)-5-(trifluoromethoxy)picolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-(trifluoromethoxy)picolinic acid [J. D. Scott et al. WO2011044181 (2011)] following General Procedure G yielded the title compound as a colorless amorphous solid. MS: m/z=481.4 [M+H]$^+$.

EXAMPLE 17

N-(3-((4S,6S)-2-Amino-4-methyl-6-(trifluoromethyl)-5,6-dihydro-4H-1,3-oxazin-4-yl)-4-fluorophenyl)-5-(difluoromethyl)picolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-(difluoromethyl)picolinic acid [J. D. Scott et al. WO2011044181 (2011)] following General Procedure G yielded the title compound as a colorless amorphous solid. MS: m/z=447.5 [M+H]$^+$.

EXAMPLE 18

N-(3-((4S,6S)-2-Amino-4-methyl-6-(trifluoromethyl)-5,6-dihydro-4H-1,3-oxazin-4-yl)-4-fluorophenyl)-5-(2,2,2-trifluoroethoxy)picolinamide The coupling of (4S,6S)-4-(5-amino-2-fluorophenyl)-4-methyl-6-(trifluoromethyl)-5,6-dihydro-4H-1,3-oxazin-2-amine (XI-1) and 5-(2,2,2-trifluoroethoxy)picolinic acid [D. Banner et al. WO2010128058 (2010)] following General Procedure G yielded the title compound as a colorless amorphous solid. MS: m/z=495.4 [M+H]$^+$.

EXAMPLE 19

N-(3-((4S,6S)-2-Amino-4-methyl-6-(trifluoromethyl)-5,6-dihydro-4H-1,3-oxazin-4-yl)-4-fluorophenyl)-5-(fluoromethyl)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 5-(fluoromethyl)pyrazine-2-carboxylic acid [J. M. Ellard et al. WO2011009898 (2011)] following

EXAMPLE 20

N-(3-((4S,6S)-2-Amino-4-methyl-6-(trifluoromethyl)-5,6-dihydro-4H-1,3-oxazin-4-yl)-4-fluorophenyl)-5-(difluoromethyl)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 5-(difluoromethyl)pyrazine-2-carboxylic acid [J. M. Ellard et al. WO2011009898 (2011)] following General Procedure F yielded the title compound as a colorless solid. MS: m/z=448.5 [M+H]$^+$.

EXAMPLE 21

N-(3-((4S,6S)-2-Amino-4-methyl-6-(trifluoromethyl)-5,6-dihydro-4H-1,3-oxazin-4-yl)-4-fluorophenyl)-5-methylpyrazine-2-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 5-methylpyrazine-2-carboxylic acid following General Procedure F yielded the title compound as a colorless amorphous solid. MS: m/z=412.5 [M+H]$^+$.

EXAMPLE 22

N-(3-((4S,6S)-2-Amino-4-methyl-6-(trifluoromethyl)-5,6-dihydro-4H-1,3-oxazin-4-yl)-4-fluorophenyl)-5-(but-2-ynyloxy)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 5-(but-2-ynyloxy)pyrazine-2-carboxylic acid [G. Csjernyik et al. WO2012087237 (2012)] following General Procedure F yielded the title compound as a white solid. MS: m/z=466.5 [M+H]$^+$.

EXAMPLE 23

N-(3-((4S,6S)-2-Amino-4-methyl-6-(trifluoromethyl)-5,6-dihydro-4H-1,3-oxazin-4-yl)-4-fluorophenyl)-5-(fluoromethoxy)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 5-(fluoromethoxy)pyrazine-2-carboxylic acid [J. M. Ellard et al. WO2011009898 (2011)] following General Procedure G yielded the title compound as a colorless amorphous solid. MS: m/z=446.5 [M+H]$^+$.

EXAMPLE 24

N-(3-((4S,6S)-2-Amino-4-methyl-6-(trifluoromethyl)-5,6-dihydro-4H-1,3-oxazin-4-yl)-4-fluorophenyl)-5-(difluoromethoxy)pyrazine-2-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 5-(difluoromethoxy)pyrazine-2-carboxylic acid [J. M. Ellard et al. WO2011009898 (2011)] following General Procedure G yielded the title compound as a colorless amorphous solid. MS: m/z=446.5 [M+H]$^+$.

EXAMPLE 25

N-(3-((4S,6S)-2-Amino-4-methyl-6-(trifluoromethyl)-5,6-dihydro-4H-1,3-oxazin-4-yl)-4-fluorophenyl)-2-(fluoromethyl)oxazole-4-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 2-(fluoromethyl)oxazole-4-carboxylic acid [D. Banner et al. WO2011069934 (2011)] following General Procedure F yielded the title compound as a colorless solid. MS: m/z=419.5 [M+H]$^+$.

EXAMPLE 26

N-(3-((4S,6S)-2-Amino-4-methyl-6-(trifluoromethyl)-5,6-dihydro-4H-1,3-oxazin-4-yl)-4-fluorophenyl)-4-chloro-1-(difluoromethyl)-1H-pyrazole-3-carboxamide The coupling of (4S,6S)-4-(5-amino-2-fluorophenyl)-4-methyl-6-(trifluoromethyl)-5,6-dihydro-4H-1,3-oxazin-2-amine (XI-1) and 4-chloro-1-(difluoromethyl)-1H-pyrazole-3-carboxylic acid [D. Banner et al. WO2011069934 (2011)] following General Procedure F yielded the title compound as an off-white solid. MS: m/z=470.4 [M+H]$^+$.

EXAMPLE 27

N-(3-((4S,6S)-2-Amino-4-(fluoromethyl)-6-(trifluoromethyl)-5,6-dihydro-4H-1,3-oxazin-4-yl)-4-fluorophenyl)-5-cyano-3-methylpicolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-cyano-3-methylpicolinic acid [S. Badiger et al. WO2011009943 (2011)] following General Procedure G yielded the title compound as a light yellow solid. MS: m/z=454.4 [M+H]$^+$.

EXAMPLE 28

N-(3-((4S,6S)-2-Amino-4-(fluoromethyl)-6-(trifluoromethyl)-5,6-dihydro-4H-1,3-oxazin-4-yl)-4-fluorophenyl)-3-chloro-5-cyanopicolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 3-chloro-5-cyanopicolinic acid following General Procedure G yielded the title compound as a light yellow solid. MS: m/z=474.4 [M+H]$^+$.

EXAMPLE 29

N-(3-((4S,6S)-2-Amino-4-(fluoromethyl)-6-(trifluoromethyl)-5,6-dihydro-4H-1,3-oxazin-4-yl)-4-fluorophenyl)-3,5-dichloropicolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 3,5-dichloropicolinic acid following General Procedure F yielded the title compound as a colorless amorphous solid. MS: m/z=430.5 [M+H]$^+$.

General Procedure G yielded the title compound as a colorless solid. MS: m/z=483.3 [M+H]⁺, 485.3 [M+2+H]⁺, 487.2 [M+4+H]⁺.

EXAMPLE 30

N-(3-((4S,6S)-2-Amino-4-(fluoromethyl)-6-(trifluoromethyl)-5,6-dihydro-4H-1,3-oxazin-4-yl)-4-fluorophenyl)-5-methoxypicolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-methoxypicolinic acid following General Procedure G yielded the title compound as an amorphous colorless solid. MS: m/z=445.5 [M+H]⁺.

EXAMPLE 31

N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethoxy)picolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(difluoromethoxy)picolinic acid following General Procedure G yielded the title compound as an amorphous colorless solid. MS: m/z=481.4 [M+H]⁺.

EXAMPLE 32

N-(3-((4S,6S)-2-Amino-4-(fluoromethyl)-6-(trifluoromethyl)-5,6-dihydro-4H-1,3-oxazin-4-yl)-4-fluorophenyl)-5-(trifluoromethoxy)picolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(trifluoromethoxy)picolinic acid following General Procedure G yielded the title compound as an amorphous colorless solid. MS: m/z=499.4 [M+H]⁺.

EXAMPLE 33

N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethyl)picolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(difluoromethyl)picolinic acid following General Procedure G yielded the title compound as an amorphous colorless solid. MS: m/z=465.4 [M+H]⁺.

EXAMPLE 34

N-(3-((4S,6S)-2-Amino-4-(fluoromethyl)-6-(trifluoromethyl)-5,6-dihydro-4H-1,3-oxazin-4-yl)-4-fluorophenyl)-5-(2,2,2-trifluoroethoxy)picolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(2,2,2-trifluoroethoxy)picolinic acid following General Procedure G yielded the title compound as an amorphous colorless solid. MS: m/z=513.4 [M+H]⁺.

EXAMPLE 35

N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethoxy)picolinamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(fluoromethoxy)picolinic acid following General Procedure G yielded the title compound as a white solid. MS: m/z=463.6 [M+H]⁺.

EXAMPLE 36

N-(3-((4S,6S)-2-Amino-4-(fluoromethyl)-6-(trifluoromethyl)-5,6-dihydro-4H-1,3-oxazin-4-yl)-4-fluorophenyl)-5-methoxypyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-methoxypyrazine-2-carboxylic acid following General Procedure F yielded the title compound as a colorless solid. MS: m/z=446.4 [M+H]⁺.

EXAMPLE 37

N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethyl)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(fluoromethyl)pyrazine-2-carboxylic acid following General Procedure F yielded the title compound as a white solid. MS: m/z=448.6 [M+H]⁺.

EXAMPLE 38

N-(3-((4S,6S)-2-Amino-4-(fluoromethyl)-6-(trifluoromethyl)-5,6-dihydro-4H-1,3-oxazin-4-yl)-4-fluorophenyl)-5-(but-2-ynyloxy)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(but-2-ynyloxy)pyrazine-2-carboxylic acid following General Procedure F yielded the title compound as a white solid. MS: m/z=484.4 [M+H]⁺.

EXAMPLE 39

N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethoxy)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(difluoromethoxy)pyrazine-2- carboxylic acid following General Procedure G yielded the title compound as a colorless solid. MS: m/z=482.6 [M+H]$^+$.

EXAMPLE 40

N-(3-((4S,6S)-2-Amino-4-(fluoromethyl)-6-(trifluoromethyl)-5,6-dihydro-4H-1,3-oxazin-4-yl)-4-fluorophenyl)-5-(2,2-difluoroethoxyl)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(2,2-difluoroethoxyl)pyrazine-2-carboxylic acid [Y. Suzuki et al. WO2009091016 (2009)] following General Procedure G yielded the title compound as a colorless solid. MS: m/z=496.6 [M+H]$^+$.

EXAMPLE 41

N-(3-((4S,6S)-2-Amino-4-(fluoromethyl)-6-(trifluoromethyl)-5,6-dihydro-4H-1,3-oxazin-4-yl)-4-fluorophenyl)-5-(2,2,2-trifluoroethoxyl)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(2,2,2-trifluoroethoxyl)pyrazine-2-carboxylic acid following General Procedure G yielded the title compound as a colorless solid. MS: m/z=514.6 [M+H]$^+$.

EXAMPLE 42

N-(3-((4S,6S)-2-Amino-4-(fluoromethyl)-6-(trifluoromethyl)-5,6-dihydro-4H-1,3-oxazin-4-yl)-4-fluorophenyl)-5-methylpyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-methylpyrazine-2-carboxylic acid following General Procedure G yielded the title compound as a colorless solid. MS: m/z=430.6 [M+H]$^+$.

EXAMPLE 43

N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethoxy)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(fluoromethoxy)pyrazine-2-carboxylic acid following General Procedure G yielded the title compound as a colorless amorphous solid. MS: m/z=464.4 [M+H]$^+$.

EXAMPLE 44

N-(3-((4S,6S)-2-Amino-4-(fluoromethyl)-6-(trifluoromethyl)-5,6-dihydro-4H-1,3-oxazin-4-yl)-4-fluorophenyl)-3-methylpyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 3-methylpyrazine-2-carboxylic acid following General Procedure G yielded the title compound as a light yellow oil. MS: m/z=430.4 [M+H]$^+$.

EXAMPLE 45

N-(3-((4S,6S)-2-Amino-4-(fluoromethyl)-6-(trifluoromethyl)-5,6-dihydro-4H-1,3-oxazin-4-yl)-4-fluorophenyl)-5-(difluoromethyl)pyrazine-2-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 5-(difluoromethyl)pyrazine-2-carboxylic acid following General Procedure F yielded the title compound as a colorless solid. MS: m/z=466.4 [M+H]$^+$.

EXAMPLE 46

N-(3-((4S,6S)-2-Amino-4-(fluoromethyl)-6-(trifluoromethyl)-5,6-dihydro-4H-1,3-oxazin-4-yl)-4-fluorophenyl)-4-chloro-1-(difluoromethyl)-1H-pyrazole-3-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 4-chloro-1-(difluoromethyl)-1H-pyrazole-3-carboxylic acid following General Procedure G yielded the title compound as a colorless solid. MS: m/z=488.5 [M+H]$^+$.

EXAMPLE 47

N-(3-((4S,6S)-2-Amino-4-(fluoromethyl)-6-(trifluoromethyl)-5,6-dihydro-4H-1,3-oxazin-4-yl)-4-fluorophenyl)-2-(fluoromethyl)oxazole-4-carboxamide The coupling of (4S,6S)-4-(5-amino-2-fluorophenyl)-4-(fluoromethyl)-6-(trifluoromethyl)-5,6-dihydro-4H-1,3-oxazin-2-amine (XI-2) and 2-(fluoromethyl)oxazole-4-carboxylic acid following General Procedure G yielded the title compound as an off-white solid. MS: m/z=437.4 [M+H]$^+$.

EXAMPLE 48

N-(3-((4S,6R)-2-Amino-4-(difluoromethyl)-6-(trifluoromethyl)-5,6-dihydro-4H-1,3-oxazin-4-yl)-4-fluorophenyl)-5-cyanopicolinamide The coupling of (4S,6R)-4-(5-amino-2-fluorophenyl)-4-(difluoromethyl)-6-(trifluoromethyl)-5,6-dihydro-4H-1,3-oxazin-2-amine (XXI-2) and 5-cyanopicolinic acid following General Procedure F yielded the title compound as a white solid. MS: m/z=458.6 [M+H]$^+$.

EXAMPLE 49

N-(3-((4S,6S)-2-Amino-4-(difluoromethyl)-6-(trifluoromethyl)-5,6-dihydro-4H-1,3-oxazin-4-yl)-4-fluorophenyl)-5-cyanopicolinamide The coupling of (4S,6S)-4-(5-amino-2-fluorophenyl)-4-(difluoromethyl)-6-(trifluoromethyl)-5,6-dihydro-4H-1,3-oxazin-2-amine (XXI-1) and 5-cyanopicolinic acid following General Procedure G yielded the title compound as a colorless solid. MS: m/z=458.4 [M+H]$^+$.

The invention claimed is:
1. A compound of formula I,

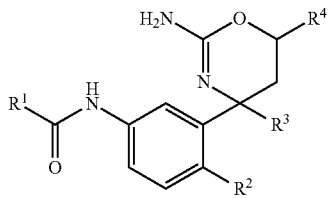

wherein
$R^1$ is selected from the group consisting of
i) aryl,
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
iii) heteroaryl, and
iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, C2-6-alkynyl-$C_{1-6}$-alkoxy, $C_{2-6}$-alkynyl and $C_{1-6}$-alkyl;
$R^2$ is selected from the group consisting of
i) hydrogen,
ii) $C_{1-6}$-alkyl, and
iii) halogen;
$R^3$ is selected from the group consisting of
i) $C_{1-6}$-alkyl, and
ii) halogen-$C_{1-6}$-alkyl,
$R^4$ is halogen-$C_{1-6}$-alkyl;
or pharmaceutically acceptable salts thereof.
2. A compound according to claim 1, wherein $R^1$ is heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl.
3. A compound according to claim 1, wherein $R^2$ is halogen.
4. A compound according to claim 2, wherein $R^2$ is halogen.
5. A compound according to claim 1, wherein $R^2$ is F.
6. A compound according to claim 2, wherein $R^2$ is F.
7. A compound according to claim 3, wherein $R^2$ is F.
8. A compound according to claim 1 wherein $R^3$ is fluoro-$C_{1-6}$-alkyl, fluoromethyl, $C_{1-6}$-alkyl.
9. A compound according to claim 2, wherein $R^3$ is fluoro-$C_{1-6}$-alkyl, fluoromethyl, $C_{1-6}$-alkyl.
10. A compound according to claim 3, wherein $R^3$ is fluoro-$C_{1-6}$-alkyl, fluoromethyl, $C_{1-6}$ alkyl.
11. A compound according to claim 4, wherein $R^3$ is fluoro-$C_{1-6}$-alkyl, fluoromethyl, $C_{1-6}$-alkyl.
12. A compound according to claim 5, wherein $R^3$ is fluoro-$C_{1-6}$-alkyl, fluoromethyl, $C_{1-6}$-alkyl.
13. A compound according to claim 6, wherein $R^3$ is fluoro-$C_{1-6}$-alkyl, fluoromethyl, $C_{1-6}$-alkyl.
14. A compound according to claim 7, wherein $R^3$ is fluoro-$C_{1-6}$-alkyl, fluoromethyl, $C_{1-6}$-alkyl.
15. A compound according to claim 1, wherein $R^3$ is methyl.
16. A compound according to claim 2, wherein $R^3$ is methyl.
17. A compound according to claim 3, wherein $R^3$ is methyl.
18. A compound according to claim 4, wherein $R^3$ is methyl.
19. A compound according to claim 5, wherein $R^3$ is methyl.
20. A compound according to claim 6, wherein $R^3$ is methyl.
21. A compound according to claim 7, wherein $R^3$ is methyl.
22. A compound according to claim 8, wherein $R^3$ is methyl.
23. A compound according to claim 9, wherein $R^3$ is methyl.
24. A compound according to claim 1, wherein $R^4$ is fluoro-$C_{1-6}$-alkyl.
25. A compound according to claim 1, wherein $R^4$ is trifluoromethyl.
26. A compound according to claim 1 of formula Ia-1

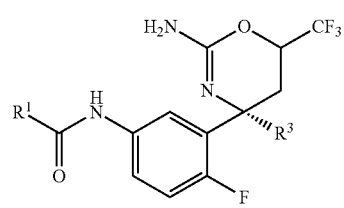

wherein
R is selected from the group consisting of
i) aryl,
ii) aryl substituted by 1-2 substituents individually selected from cyano, cyano-$C_{1-6}$- alkyl, halogen, halogen-$C_{1-6}$-alkoxy, halogen-$C_{1-6}$-alkyl, $C_{1-6}$-alkoxy, $C_{1-6}$-alkoxy-$C_{1-6}$- alkyl, $C_{2-6}$-alkynyl-$C_{1-6}$-alkoxy, $C_{2-6}$-alkynyl and $C_{1-6}$-alkyl,
iii) heteroaryl, and
iv) heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl; and
$R^3$ is selected from the group consisting of
i) $C_{1-6}$-alkyl, and
ii) halogen-$C_{1-6}$-alkyl,
or pharmaceutically acceptable salts thereof.
27. A compound according to claim 1, wherein $R^1$ is heteroaryl substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.
28. A compound according to claim 27, wherein $R^1$ is heteroaryl substituted by 1-2 substituents individually selected from cyano, halogen, halogen-$C_{1-6}$-alkoxy, halogen-$C_{1-6}$-alkyl, $C_{1-6}$-alkoxy, $C_{2-6}$-alkynyl-$C_{1-6}$-alkoxy and $C_{1-6}$-alkyl.
29. A compound according to claim 28, wherein $R^1$ is heteroaryl substituted by 1-2 substituents individually selected from cyano, halogen, halogen-$C_{1-6}$-alkoxy and $C_{1-6}$-alkoxy.
30. A compound according to claim 1, wherein $R^1$ is 1-(difluoromethyl)-1H-pyrazole-3-yl, 2-(fluoromethyl)oxazole-4-yl, 3,5-dichloro-pyridin-2-yl, 3-chloro-5-cyanopyridin-2-yl, 3-methylpyrazine-2-yl, 4-chloro-1-(difluoromethyl)-1H-pyrazole-3-yl, 5-(2,2,2-trifluoroethoxyl)pyrazine-2-yl, 5-(2, 2-difluoroethoxyl)pyrazine-2-yl, 5-(but-2-ynyloxy) pyrazine-2-yl, 5-(difluoromethoxy)pyrazine-2-yl, 5-(difluoromethyl)pyrazine-2-yl, 5-(fluoromethoxy)pyrazine-2-yl, 5-(fluoromethyl)pyrazine-2-yl, 5-chloro-pyridin-2-yl, 5-cyano-3-methyl-pyridin-2-yl, 5-cyano-pyridin-2-yl, 5-difluoromethoxy-pyrazin-2-yl, 5-difluoromethoxy-pyridin-2-yl, 5-difluoromethyl-pyridin-2-yl, 5-fluoromethoxy-pyridin-2-yl, 5-methoxy-pyrazin-2-yl, 5-methoxy-pyridin-2-yl, 5-methyl-pyrazine-2-yl, 5-trifluoroethoxy-pyridin-2-yl, 5trifluoromethoxy-pyrazin-2-yl or 5-trifluoromethoxy- pyridin-2-yl.

31. A compound according to claim 30, wherein R$^1$ is 1-(difluoromethyl)-1H-pyrazole-3-yl, 2-(fluoromethyl)oxazole-4-yl, 3,5-dichloro-pyridin-2-yl, 3-chloro-5- cyanopyridin-2-yl, 3-methylpyrazine-2-yl, 4-chloro-1-(difluoromethyl)-1H-pyrazole-3-yl, 5-(2,2,2-trifluoroethoxy)pyrazine-2-yl, 5-(2,2-difluoroethoxy)pyrazine-2-yl, 5-(but-2-ynyloxy)pyrazine-2-yl, 5-(difluoromethoxy)pyrazine-2-yl, 5-(difluoromethyl)pyrazine-2-yl, 5-(fluoromethoxy)pyrazine-2-yl, 5-(fluoromethyl)pyrazine-2-yl, 5-chloro-pyridin-2-yl, 5- cyano-3-methyl-pyridin-2-yl, 5-cyano-pyridin-2-yl, 5-difluoromethoxy-pyrazin-2-yl, 5- difluoromethoxy-pyridin-2-yl, 5-difluoromethyl-pyridin-2-yl, 5-fluoromethoxy-pyridin-2-yl, 5-methoxy-pyrazin-2-yl, 5-methoxy-pyridin-2-yl, 5-methyl-pyrazine-2-yl, 5- trifluoroethoxy-pyridin-2-yl, 5-trifluoromethoxy-pyrazin-2-yl or 5-trifluoromethoxy-pyridin-2-yl.

32. A compound according to claim 1, wherein R$^1$ is 5-cyano-pydidin-2-yl, 5- chloro-pydidin-2-yl, 5-(2,2-difluoroethoxy)pyrazine-2-yl, 542,2,2-trifluoroethoxy)pyrazine-2-yl or 5-methoxypyrazine-2-yl.

33. A compound according to claim 32, wherein R$^1$ is 1-(difluoromethyl)-1H- pyrazole-3-yl, 2-(fluoromethyl)oxazole-4-yl, 3,5-dichloro-pyridin-2-yl, 3-chloro-5- cyanopyridin-2-yl, 3-methylpyrazine-2-yl, 4-chloro-1-(difluoromethyl)-1H-pyrazole-3-yl, 5-(2,2,2-trifluoroethoxy)pyrazine-2-yl, 5-(2,2-difluoroethoxy)pyrazine-2-yl, 5-(but-2-ynyloxy)pyrazine-2-yl, 5-(difluoromethoxy)pyrazine-2-yl, 5-(difluoromethyl)pyrazine-2-yl, 5-(fluoromethoxy)pyrazine-2-yl, 5-(fluoromethyl)pyrazine-2-yl, 5-chloro-pyridin-2-yl, 5- cyano-3-methyl-pyridin-2-yl, 5-cyano-pyridin-2-yl, 5-difluoromethoxy-pyrazin-2-yl, 5- difluoromethoxy-pyridin-2-yl, 5-difluoromethyl-pyridin-2-yl, 5-fluoromethoxy-pyridin-2-yl, 5-methoxy-pyrazin-2-yl, 5-methoxy-pyridin-2-yl, 5-methyl-pyrazine-2-yl, 5- trifluoroethoxy-pyridin-2-yl, 5-trifluoromethoxy-pyrazin-2-yl or 5-trifluoromethoxy-pyridin-2-yl.

34. A compound according to claim 1, wherein R$^1$ is 5-cyano-pyridin-2-yl.

35. A compound according to claim 1, wherein said compound is selected from the group consisting of:
N-(3-((4S,6S)-2-amino-4-methyl-6-(trifluoromethyl)-5,6-dihydro-4H-1,3-oxazin-4-yl)-4-fluorophenyl)-5-cyanopicolinamide, N-(3-((4S,6S)-2-amino-4-methyl-6-(trifluoromethyl)-5,6-dihydro-4H-1,3-oxazin-4-yl)-4-fluorophenyl)-5-chloropicolinamide, N-(3-((4S,6S)-2-amino-4-(fluoromethyl)-6-(trifluoromethyl)-5,6-dihydro-4H-1,3-oxazin-4-yl)-4-fluorophenyl)-5-cyanopicolinamide, N-(3-((4S,6S)-2-amino-4-(fluoromethyl)-6-(trifluoromethyl)-5,6-dihydro-4H-1,3-oxazin-4-yl)-4-fluorophenyl)-5-chloropicolinamide, N-(3-((4S,6S)-2-amino-4-methyl-6-(trifluoromethyl)-5,6-dihydro-4H-1,3-oxazin-4-yl)-4-fluorophenyl)-5-methoxypyrazine-2-carboxamide, N-(3-((4S,6S)-2-amino-4-methyl-6-(trifluoromethyl)-5,6-dihydro-4H-1,3-oxazin-4-yl)-4-fluorophenyl)-5-(2,2-difluoroethoxy)pyrazine-2-carboxamide, N-(3-((4S,6S)-2-amino-4-methyl-6-(trifluoromethyl)-5,6-dihydro-4H-1,3-oxazin-4-yl)-4-fluorophenyl)-5-(2,2,2-trifluoroethoxy)pyrazine-2-carboxamide, N-(3-((4S,6R)-2-Amino-4-methyl-6-(trifluoromethyl)-5,6-dihydro-4H-1,3-oxazin-4-yl)-4-fluorophenyl)-5-cyanopicolinamide, N-(3-((4S,6R)-2-Amino-4-methyl-6-(trifluoromethyl)-5,6-dihydro-4H-1,3-oxazin-4-yl)-4-fluorophenyl)-5-chloropicolinamide, N-(3-((4S,6S)-2-Amino-4-methyl-6-(trifluoromethyl)-5,6-dihydro-4H-1,3-oxazin-4-yl)-4-fluorophenyl)-3,5-chloropicolinamide, N-(3-((4S,6S)-2-Amino-4-methyl-6-(trifluoromethyl)-5,6-dihydro-4H-1,3-oxazin-4-yl)-4-fluorophenyl)-5- (fluoromethoxy)picolinamide, N-(3-((4S,6S)-2-Amino-4-methyl-6-(trifluoromethyl)-5,6-dihydro-4H-1,3-oxazin-4-yl)-4-fluorophenyl)-5-cyano-3-methylpicolinamide, N-(3- ((4,6S)-2-Amino-4-methyl-6-(trifluoromethyl)-5,6-dihydro-4H-1,3-oxazin-4-yl)-4- fluorophenyl)-3-chloro-5-cyanopicolinamide, N-(3-((4S,6S)-2-Amino-4-methyl-6-(trifluoromethyl)-5,6-dihydro-4H-1,3-oxazin-4-yl)-4-fluorophenyl)-5-methoxypicolinamide, N-(3-((4S,6S)-2-Amino-4-methyl-6-(trifluoromethyl)-5,6-dihydro-4H-1,3-oxazin-4-yl)-4-fluorophenyl)-5-(difluoromethoxy)picolinamide, N-(3-((4S,6S)-2-Amino-4-methyl-6-(trifluoromethyl)-5,6-dihydro-4H-1,3-oxazin-4-yl)-4-fluorophenyl-(trifluoromethoxy)picolinamide, N-(3-((4S,6S)-2-Amino-4-methyl-6-(trifluoromethyl)-5,6-dihydro-4H-1,3-oxazin-4-yl)-4-fluorophenyl)-5-(difluoromethyl)picolinamide, N-(3-((4S,6S)-2-Amino-4-methyl-6-(trifluoromethyl)-5,6-dihydro-4H-1,3-oxazin-4-yl)-4-fluorophenyl)-5-(2,2,2-trifluoroethoxy)picolinamide, N-(3-((4S,6S)-2-Amino-4-methyl-6-(trifluoromethyl)-5,6-dihydro-4H-1,3oxazin-4-yl)-4-fluorophenyl)-5-(fluoromethyl)pyrazine-2-carboxamide, N-(3-((4S,6S )-2-Amino-4-methyl-6-(trifluoromethyl)-5,6-dihydro-4H-1,3-oxazin-4-yl)-4-fluorophenyl)-5-(difluoromethyl)pyrazine-2-carboxamide, N-(3-((4S,6S )-2-Amino-4-methyl-6-(trifluoromethyl)-5,6-dihydro-4H-1,3-oxazin-4-yl)-4-fluorophenyl)-5-methylpyrazm carboxamide, N-(3-((4S,6S )-2-Amino-4-methyl-6-(trifluoromethyl)-5,6-dihydro-4H-1,3-oxazin-4-yl)-4-fluorophenyl)-5-(but-2-ynyloxy)pyrazine-2-carboxamide, N-(3 4-((4S,6S )-2-Amino-4-methyl-6-(trifluoromethyl)-5,6-dihydro-4H-1,3-oxazin-4-yl)-4-fluorophe(fluoromethoxy)pyrazine-2-carboxamide, N-(3-((4S,6S)-2-Amino-4-methyl-6-(trifluoromethyl)-5,6-dihydro-4H-1,3-oxazin-4-yl)-4-fluorophenyl)-5-(difluoromethoxy)pyrazine-2-carboxamide, N-(3-((4S,6S )-2-Amino-4-methyl-6-(trifluoromethyl)-5,6-dihydro-4H-1,3-oxazin-4-yl)-4-fluorophenyl)-2-(fluoromethyl)oxazole-4-carboxamide, N-(3-((4S,6S)-2-Amino-4-methyl-6-(trifluoromethyl)-5,6-dihydro-4H-1,3-oxazin-4-yl)-4-fluorophenyl)-4-chloro-1-(difluoromethyl)-1H-pyrazole-3-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-cyano-3-methylpicolinamide, N-(3-((4S,6S )-2-Amino-4-(fluoromethyl)-6-(trifluoromethyl)-5,6-dihydro-4H-1,3-oxazin-4-yl)-4-fluorophenyl)-3-chloro-5-cyanopicolinamide, N-(3 4-((4S,6S )-2-Amino-4-(fluoromethyl)-6-(tri-4-fluorophenyl)-3,5-dichloropicolinamide, N-(3-((4S,6S )-2-Amino-4-(fluoromethyl)-6-(trifluoromethyl)-5,6-dihydro-4H-1,3-oxazin-4-yl)-4-fluorophenyl)-5methoxypicolinamide, N-(3-((4S,6S )-2-Amino-4-(fluoromethyl)-6-(trifluoromethyl)-5,6-dihydro-4H-1, 3-oxazin-4-yl)-4-fluorophenyl)-5-(difluoromethoxy) picolinamide, N-(3-((4S,6S )-2-Amino-4-(fluoromethyl)-6-(tri-4-fluorophenyl)-5-(trifluoromethoxy)picolinamide, N-(3-((4S,6S )-2-Amino-4-(fluoromethyl)-6-(trifluoromethyl)-5-(difluoromethyl)picolinamide, N-(3 4-((4S,6S )-2-Amino-4-(fluoromethyl)-6-(trifluoromethyl)-5,6-dihydro-4H-1,3-oxazin-4-yl)-4-fluorophenyl)-5-(2,2,2-trifluoroethoxy)picolinamide, N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethoxy) picolinamide, N-(3-((4S,6S )-2-Amino-4-(fluoromethyl)-6-(trifluoromethyl)-5,6-dihydro-4H-1,3-oxazin-4-yl)-4-fluorophenyl)-5-methoxypycarboxamide, N-(3-((4S,6S )-2-Amino-4-(fluoromethyl)-6-(trifluoromethyl)-5,6-dihydro-4H-1,3-oxazin-4-yl)-4-fluorophenyl)-5-(fluoromethyl) ypyrazine-2-carboxamide, N-(3-((4S,6S )-2-Amino-4-(fluoromethyl)-6-(trifluoromethyl)-5,6-dihydro-4H-1,3-oxazin-4 4-fluorophenyl)-5-(but-2-ynyloxy) pyrazine-2-carboxamide, N-(3-((4S,6S )-2-Amino-4-(fluoromethyl)-6-(trifluoromethyl)-5,6-dihydro-4H-1,3-oxazin-4-yl)-4-fluorophenyl)-5-(difluoromethoxy) pyrazine-2-carboxamide, N-(3-((4S,6S )-2-Amino-4-(fluoromethyl)-6-(trifluoromethyl)-5,6-dihydro-4H-1,3-oxazin-4-yl)-4-fluorophenyl)-5-(2,2-difluoroethoxy) pyrazine-2-carboxamide, N-(3-((4S,6S )-2-Amino-4-(fluoromethyl)-6-(trifluoromethyl)-5,6-dihydro-4H-1,3-oxazin-4-yl)-4-fluorophenyl)-5-(2,2,2-trifluoroethoxy)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-methylpyrazin carboxamide, N-(3-((4S,6S)-2-Amino-4-(fluoromethyl)-6-(trifluoromethyl)-5,6-dihydro-4H-1,3-oxazin-4-yl)-4-fluorophenyl)-5-(fluoromethoxy) pyrazine-2-carboxamide, N-(3-((4S,6S)-2-Amino-4-(fluoromethyl)-6-(trifluoromethyl)-5,6-dihydro-4H-1,3-oxazin-4-fluorophenyl)-3-methylpyrazine-2-carboxamide, N-(3-((4S,6S)-2-Amino-4-(fluoromethyl)-6-(trifluoromethyl)-5,6-dihydro-4H-1,3-oxazin-4-yl)-4-fluoroph-(difluoromethyl)pyrazine-2-carboxamide, N-(3-((4S,6S)-2-Amino-4-(fluoromethyl)-6-(trifluoromethyl)-5,6-dihydro-4H-1,3-oxazin-4-yl)-4-fluorophenyl)-4-chloro-1-(difluoromethyl)-1H-pyrazole-3-carboxamide, N-(3-((4S,6S)-2-Amino-4-(fluoromethyl)-6-(trifluoromethyl)-5,6-dihydro-4H-1,3-oxazin-4-yl)-4-fluorophenyl)-2-(fluoromethyl)oxazole-4-carboxamide, N-(3-((4S,6R)-2-Amino-4-(difluoromethyl)-6-(trifluoromethyl)-5,6-dihydro-4H-1,3-oxazin-4-yl)-4-fluorophenyl)-5-cyanopicolinam and N-(3-44S,6S)-2-Amino-4-(difluoromethyl)-6-(trifluoromethyl)-5,6-dihydro-4H-1,3-oxazin-4-yl)-4-fluorophenyl)-5-cyanopico linamide, or a pharmaceutically acceptable salt thereof.

36. A compound according to claim 1, wherein said compound is selected from the group consisting of N-(3-((4S,6S -2-amino-4-methyl-6-(trifluoromethyl)-5,6-dihydro-4H-1,3-oxazin-4-yl)-4-fluorophenyl 5-cyanopico linamide, N-(3-((4S,6S -2-amino-4-methyl-6-(trifluoromethyl)-5,6-dihydro -4H-1,3-oxazin-4-yl)-4-fluorophenyl 5-chloropico linamide, N-(3-((4S,6S-2-amino-4-(fluoromethyl)-6-(trifluoromethyl)-5, 6-dihydro-4H-1,3-oxazine-4-yl)-4-fluorophenyl 5-cyanopico linamide, N-(3-((4S,6S -2-amino-4-(fluoromethyl)-6-(trifluoromethyl)-5, 6-dihydro-4H-1,3-oxazine-4-yl)-4-fluorophenyl 5-chloropico linamide, N-(3-((4S,6S -2-amino-4-methyl-6-(trifluoromethyl)-5,6-dihydro-4H-1,3-oxazin-4-yl)-4-fluorophenyl 5-methoxypyrazine-2-carboxamide, N-(3-((4S,6S -2-amino-4-methyl-6-(trifluoromethyl)-5,6-dihydro-4H-1,3-oxazin-4-yl)-4-fluorophenyl 5-(2,2-difluoroethoxy)pyrazine-2-carboxamide, and N-(3-((4S,6S)-2-amino-4-methyl-6-(trifluoromethyl)-5, 6-dihydro-4H-1,3-oxazin-4-yl)-4-fluorophenyl)-5-(2,2, 2-trifluoroethoxy)pyrazine-2-carboxamide, or a pharmaceutically acceptable salt thereof.

37. A process for preparing a compound of formula I, which process comprises reacting a compound of formula XI' with a compound of formula XII:

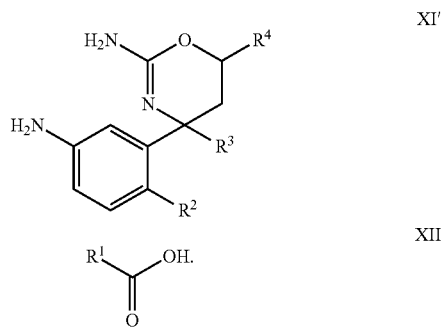

38. A pharmaceutical composition comprising:
a compound according to claim 1 and a pharmaceutically acceptable carrier and/or a pharmaceutically acceptable auxiliary substance.

39. A method for the therapeutic treatment of Alzheimer's disease or amyotrophic lateral sclerosis (ALS), arterial thrombosis, myocardial infarction, stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, Spinocerebellar Ataxia 1, Spinocerebellar Ataxia 7, Whipple's Disease or Wilson's Disease, said method comprising: administering a compound according to claim 1 to a human being or animal in need thereof.

* * * * *